United States Patent
Bar-El et al.

(10) Patent No.: US 10,149,943 B2
(45) Date of Patent: Dec. 11, 2018

(54) LINEAR ROTATION STABILIZER FOR A TELESCOPING SYRINGE STOPPER DRIVERDRIVING ASSEMBLY

(71) Applicant: MEDIMOP Medical Projects Ltd., Ra'anana (IL)

(72) Inventors: Yossi Bar-El, Beit Arye (IL); Gil Yigal, Gan Yavne (IL); Reuven Y. Filman, Netanya (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 577 days.

(21) Appl. No.: 14/725,009

(22) Filed: May 29, 2015

(65) Prior Publication Data
US 2016/0346478 A1    Dec. 1, 2016

(51) Int. Cl.
*A61M 5/315*    (2006.01)
*A61M 5/20*    (2006.01)
*A61M 5/145*    (2006.01)

(52) U.S. Cl.
CPC ...... *A61M 5/31505* (2013.01); *A61M 5/1452* (2013.01); *A61M 5/20* (2013.01);
(Continued)

(58) Field of Classification Search
CPC .......... A61M 5/31505; A61M 5/31576; A61M 5/20; A61M 5/1452; A61M 5/31511;
(Continued)

(56) References Cited

U.S. PATENT DOCUMENTS

| 232,432 A | 9/1880 | Alison |
| 1,795,630 A | 3/1931 | Wilson |

(Continued)

FOREIGN PATENT DOCUMENTS

| CN | 1505535 A | 6/2004 |
| CN | 1747683 A | 3/2006 |

(Continued)

OTHER PUBLICATIONS

Office Action dated Sep. 9, 2015 in U.S. Appl. No. 13/643,470 by Alon.
(Continued)

*Primary Examiner* — Lauren P Farrar
(74) *Attorney, Agent, or Firm* — Panitch Schwarze Belisario & Nadel LLP

(57) ABSTRACT

A cartridge interface assembly drives a stopper in a drug reservoir or a drug delivery device. An anti-rotational guide optionally moves along an axis of a cavity of the reservoir. The anti-rotational guide is optionally slidably anti-rotationally coupled to a housing of the drug delivery device. A telescoping plunger driver may include a proximal shaft and distal shaft that telescope by relative rotation. The distal shaft is optionally slidably anti-rotationally coupled to the anti-rotational guide. The shafts are optionally oriented along said axis. In some embodiments, rotating the proximal shaft with respect to the anti-rotational guide moves the guide along said axis with respect to the housing and moves the distal shaft along the axis with respect to the anti-rotational guide.

9 Claims, 14 Drawing Sheets

(52) U.S. Cl.
CPC ...... *A61M 5/2053* (2013.01); *A61M 5/31511* (2013.01); *A61M 5/31576* (2013.01); *A61M 2005/31588* (2013.01); *A61M 2205/8206* (2013.01)

(58) Field of Classification Search
CPC ........ A61M 5/2053; A61M 2205/8206; A61M 2005/31588
See application file for complete search history.

(56) References Cited

U.S. PATENT DOCUMENTS

| | | |
|---|---|---|
| 2,677,373 A | 5/1954 | Barradas |
| 2,702,547 A | 2/1955 | Glass |
| 2,860,635 A | 11/1958 | Wilburn |
| 3,203,269 A | 8/1965 | Perrine |
| 3,212,685 A | 10/1965 | Richard et al. |
| 3,623,474 A | 11/1971 | Heilman et al. |
| 3,794,028 A | 2/1974 | Mueller et al. |
| 3,994,295 A | 11/1976 | Wulff |
| 4,195,636 A | 4/1980 | Behnke |
| 4,218,724 A | 8/1980 | Kaufman |
| 4,254,768 A | 3/1981 | Ty |
| 4,273,122 A | 6/1981 | Whitney et al. |
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,502,488 A | 3/1985 | Degironimo et al. |
| 4,504,263 A | 3/1985 | Steuer et al. |
| 4,564,054 A | 1/1986 | Gustaysson |
| 4,565,543 A | 1/1986 | Bekkering et al. |
| 4,585,439 A | 4/1986 | Michel |
| 4,599,082 A | 7/1986 | Grimard |
| 4,601,702 A | 7/1986 | Hudson |
| 4,664,654 A | 5/1987 | Strauss |
| 4,685,903 A | 8/1987 | Cable et al. |
| 4,698,055 A | 10/1987 | Sealfon |
| 4,735,311 A | 4/1988 | Lowe et al. |
| 4,810,215 A | 3/1989 | Kaneko |
| 4,850,966 A | 7/1989 | Grau et al. |
| 4,867,743 A | 9/1989 | Vaillancourt |
| 4,882,575 A | 11/1989 | Kawahara |
| 4,886,499 A | 12/1989 | Cirelli et al. |
| 4,892,521 A | 1/1990 | Laico et al. |
| 4,919,596 A | 4/1990 | Slate et al. |
| 4,929,241 A | 5/1990 | Kulli |
| 4,950,246 A | 8/1990 | Muller |
| 4,964,866 A | 10/1990 | Szwarc |
| 5,051,109 A | 9/1991 | Simon |
| D322,671 S | 12/1991 | Szwarc |
| 5,109,850 A | 5/1992 | Blanco et al. |
| 5,112,317 A | 5/1992 | Michel |
| 5,131,816 A | 7/1992 | Brown et al. |
| 5,190,521 A | 3/1993 | Hubbard et al. |
| 5,254,096 A | 10/1993 | Rondelet et al. |
| 5,300,045 A | 4/1994 | Plassche, Jr. |
| 5,318,522 A | 6/1994 | D'Antonio |
| 5,342,313 A | 8/1994 | Campbell et al. |
| 5,348,544 A | 9/1994 | Sweeney et al. |
| 5,366,498 A | 11/1994 | Brannan et al. |
| 5,383,865 A | 1/1995 | Michel |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,624 A | 10/1996 | Righi et al. |
| 5,562,686 A | 10/1996 | Sauer et al. |
| 5,593,390 A | 1/1997 | Castellano et al. |
| 5,616,132 A | 4/1997 | Newman |
| 5,624,400 A | 4/1997 | Firth et al. |
| 5,637,095 A | 6/1997 | Nason et al. |
| 5,643,218 A | 7/1997 | Lynn et al. |
| 5,645,530 A | 7/1997 | Boukhny et al. |
| 5,645,955 A | 7/1997 | Maglica |
| 5,647,853 A | 7/1997 | Feldmann et al. |
| 5,658,256 A | 8/1997 | Shields |
| 5,662,678 A | 9/1997 | Macklin |
| 5,672,160 A | 9/1997 | Osterlind et al. |
| 5,690,618 A | 11/1997 | Smith et al. |
| 5,728,075 A | 3/1998 | Levander |
| D393,314 S | 4/1998 | Meisner et al. |
| 5,766,186 A | 6/1998 | Faraz et al. |
| 5,795,675 A | 8/1998 | Maglica |
| 5,800,420 A | 9/1998 | Gross et al. |
| 5,807,375 A | 9/1998 | Gross et al. |
| 5,810,784 A | 9/1998 | Tamaro |
| 5,814,020 A | 9/1998 | Gross |
| 5,830,187 A | 11/1998 | Kriesel et al. |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,893,842 A | 4/1999 | Imbert |
| 5,894,015 A | 4/1999 | Rechtin |
| 5,919,167 A | 7/1999 | Mulhauser et al. |
| 5,926,596 A | 7/1999 | Edwards et al. |
| 5,931,814 A | 8/1999 | Alex et al. |
| 5,941,850 A | 8/1999 | Shah et al. |
| 5,944,699 A | 8/1999 | Barrelle et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,989,221 A | 11/1999 | Hjertman |
| 5,993,423 A | 11/1999 | Choi |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,045,533 A | 4/2000 | Kriesel et al. |
| 6,064,797 A | 5/2000 | Crittendon et al. |
| 6,074,369 A | 6/2000 | Sage et al. |
| 6,186,982 B1 | 2/2001 | Gross et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,270,481 B1 | 8/2001 | Mason et al. |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 | 4/2002 | Garde et al. |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,554,800 B1 | 4/2003 | Nezhadian et al. |
| 6,558,351 B1 | 5/2003 | Steil et al. |
| 6,565,541 B2 | 5/2003 | Sharp |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |

(56) References Cited

U.S. PATENT DOCUMENTS

| | | |
|---|---|---|
| 6,679,862 B2 | 1/2004 | Diaz et al. |
| 6,689,118 B2 | 2/2004 | Alchas et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,787 B1 | 6/2004 | Causey, III et al. |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,960,192 B1 | 11/2005 | Flaherty et al. |
| 6,997,727 B1 | 2/2006 | Legrady et al. |
| 7,001,360 B2 | 2/2006 | Veasey et al. |
| 7,033,338 B2 | 4/2006 | Vilks et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,066,909 B1 | 6/2006 | Peter et al. |
| 7,097,637 B2 | 8/2006 | Triplett et al. |
| 7,128,727 B2 | 10/2006 | Flaherty et al. |
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| 7,291,132 B2 | 11/2007 | DeRuntz et al. |
| 7,291,159 B2 | 11/2007 | Schmelzeisen-Redeker et al. |
| 7,303,549 B2 | 12/2007 | Flaherty et al. |
| 7,344,385 B2 | 3/2008 | Chen |
| 7,364,570 B2 | 4/2008 | Gerondale et al. |
| 7,390,314 B2 | 6/2008 | Stutz, Jr. et al. |
| 7,407,493 B2 | 8/2008 | Cane' |
| D578,210 S | 10/2008 | Muta et al. |
| 7,442,186 B2 | 10/2008 | Blomquist |
| 7,455,663 B2 | 11/2008 | Bikovsky |
| 7,465,290 B2 | 12/2008 | Reilly |
| 7,488,181 B2 | 2/2009 | van Haaster |
| 7,497,842 B2 | 3/2009 | Diaz et al. |
| 7,501,587 B2 | 3/2009 | English |
| 7,503,786 B2 | 3/2009 | Kato et al. |
| 7,530,964 B2 | 5/2009 | Lavi et al. |
| 7,540,858 B2 | 6/2009 | DiBiasi |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,903 B2 | 5/2010 | Estes et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,766,867 B2 | 8/2010 | Lynch et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,794,426 B2 | 9/2010 | Briones et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,105,293 B2 | 1/2012 | Pickhard |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,177,749 B2 | 5/2012 | Slate et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,348,898 B2 | 1/2013 | Cabiri |
| 8,372,039 B2 | 2/2013 | Mernoe et al. |
| 8,373,421 B2 | 2/2013 | Lindegger et al. |

(56) References Cited

U.S. PATENT DOCUMENTS

| | | |
|---|---|---|
| 8,409,142 B2 | 4/2013 | Causey et al. |
| 8,414,557 B2 | 4/2013 | Istoc et al. |
| 8,425,468 B2 | 4/2013 | Weston |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,512,295 B2 | 8/2013 | Evans et al. |
| 8,517,987 B2 | 8/2013 | Istoc et al. |
| 8,523,803 B1 | 9/2013 | Favreau |
| 8,551,046 B2 | 10/2013 | Causey et al. |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,622,966 B2 | 1/2014 | Causey et al. |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,915,882 B2 | 12/2014 | Cabiri |
| 8,920,374 B2 | 12/2014 | Bokelman et al. |
| 8,979,802 B2 | 3/2015 | Woehr |
| 9,011,164 B2 | 4/2015 | Filman et al. |
| 9,061,104 B2 | 6/2015 | Daniel |
| 9,061,110 B2 | 6/2015 | Avery et al. |
| 9,072,827 B2 | 7/2015 | Cabiri |
| 9,089,475 B2 | 7/2015 | Fangrow |
| 9,089,641 B2 | 7/2015 | Kavazov |
| 9,149,575 B2 | 10/2015 | Cabiri |
| 9,173,997 B2 | 11/2015 | Gross et al. |
| D747,799 S | 1/2016 | Norton et al. |
| 9,259,532 B2 | 2/2016 | Cabiri |
| 9,314,569 B2 | 4/2016 | Causey et al. |
| 9,345,836 B2 | 5/2016 | Cabin et al. |
| 9,350,634 B2 | 5/2016 | Fadell |
| 9,393,365 B2 | 7/2016 | Cabiri |
| 9,421,323 B2 | 8/2016 | Cabiri et al. |
| 9,452,261 B2 | 9/2016 | Alon |
| 9,522,234 B2 | 12/2016 | Cabiri |
| 9,539,388 B2 | 1/2017 | Causey et al. |
| 9,572,926 B2 | 2/2017 | Cabiri |
| 9,656,019 B2 | 5/2017 | Cabiri et al. |
| 9,782,545 B2 | 10/2017 | Gross et al. |
| 2001/0018937 A1 | 9/2001 | Nemoto |
| 2001/0025168 A1 | 9/2001 | Gross et al. |
| 2001/0034502 A1 | 10/2001 | Moberg et al. |
| 2001/0041869 A1 | 11/2001 | Causey et al. |
| 2002/0010423 A1 | 1/2002 | Gross et al. |
| 2002/0016569 A1 | 2/2002 | Critchlow et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0065488 A1 | 5/2002 | Suzuki et al. |
| 2002/0107487 A1 | 8/2002 | Preuthun |
| 2002/0123740 A1 | 9/2002 | Flaherty et al. |
| 2002/0151855 A1 | 10/2002 | Douglas et al. |
| 2002/0161332 A1 | 10/2002 | Ramey |
| 2002/0169215 A1 | 11/2002 | Meng |
| 2003/0009133 A1 | 1/2003 | Ramey |
| 2003/0014018 A1 | 1/2003 | Giambattista et al. |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2003/0216683 A1 | 11/2003 | Shekalim |
| 2004/0000818 A1* | 1/2004 | Preuthun ........... A61M 5/14566 310/83 |
| 2004/0010207 A1 | 1/2004 | Flaherty et al. |
| 2004/0049160 A1 | 3/2004 | Hsieh et al. |
| 2004/0049161 A1 | 3/2004 | Shearn |
| 2004/0082911 A1 | 4/2004 | Tiu et al. |
| 2004/0092873 A1 | 5/2004 | Moberg |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0186441 A1 | 9/2004 | Graf et al. |
| 2004/0210196 A1 | 10/2004 | Bush, Jr. et al. |
| 2004/0260233 A1 | 12/2004 | Garibotto et al. |
| 2005/0033234 A1 | 2/2005 | Sadowski et al. |
| 2005/0038391 A1 | 2/2005 | Wittland et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | Dilanni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0095014 A1 | 5/2006 | Ethelfeld |
| 2006/0122577 A1 | 6/2006 | Poulsen et al. |
| 2006/0124269 A1 | 6/2006 | Miyazaki et al. |
| 2006/0173406 A1 | 8/2006 | Hayes et al. |
| 2006/0173439 A1 | 8/2006 | Thorne et al. |
| 2006/0195029 A1 | 8/2006 | Shults et al. |
| 2006/0206054 A1 | 9/2006 | Shekalim |
| 2006/0211982 A1 | 9/2006 | Prestrelski et al. |
| 2006/0229569 A1 | 10/2006 | Lavi et al. |
| 2006/0264888 A1 | 11/2006 | Moberg et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0025879 A1 | 2/2007 | Vandergaw |
| 2007/0049865 A1 | 3/2007 | Radmer et al. |
| 2007/0073228 A1 | 3/2007 | Mernoe et al. |
| 2007/0118405 A1 | 5/2007 | Campbell et al. |
| 2007/0167912 A1 | 7/2007 | Causey et al. |
| 2007/0179444 A1 | 8/2007 | Causey et al. |
| 2007/0185449 A1 | 8/2007 | Mernoe |
| 2007/0197954 A1 | 8/2007 | Keenan |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |

(56) References Cited

U.S. PATENT DOCUMENTS

| | | |
|---|---|---|
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215013 A1 | 9/2008 | Felix-Faure |
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319383 A1 | 12/2008 | Byland et al. |
| 2008/0319416 A1 | 12/2008 | Yodfat et al. |
| 2009/0012478 A1 | 1/2009 | Weston |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076383 A1 | 3/2009 | Toews et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093763 A1 | 4/2009 | Gonnelli et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0124977 A1 | 5/2009 | Jensen |
| 2009/0143730 A1 | 6/2009 | De Polo et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299288 A1 | 12/2009 | Sie et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0049144 A1 | 2/2010 | McConnell et al. |
| 2010/0057057 A1 | 3/2010 | Hayter et al. |
| 2010/0076382 A1 | 3/2010 | Weston |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0092915 A1 | 4/2011 | Olson et al. |
| 2011/0112504 A1 | 5/2011 | Causey et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178463 A1 | 7/2011 | Cabiri |
| 2011/0178472 A1 | 7/2011 | Cabiri |
| 2011/0201998 A1 | 8/2011 | Pongpairochana et al. |
| 2011/0224616 A1 | 9/2011 | Slate et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022496 A1 | 1/2012 | Causey et al. |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041387 A1 | 2/2012 | Bruggemann et al. |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0172817 A1 | 7/2012 | Bruggemann et al. |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0190693 A1 | 7/2013 | Ekman et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0267895 A1 | 10/2013 | Hemmingsen |
| 2013/0296799 A1 | 11/2013 | Degtiar et al. |
| 2013/0304021 A1* | 11/2013 | Cabiri ............... A61M 5/31511 604/506 |
| 2013/0310753 A1 | 11/2013 | Cabiri |
| 2013/0323699 A1 | 12/2013 | Edwards et al. |
| 2013/0331791 A1 | 12/2013 | Gross et al. |

(56) References Cited

U.S. PATENT DOCUMENTS

| | | |
|---|---|---|
| 2013/0338584 A1 | 12/2013 | Mounce et al. |
| 2014/0018735 A1 | 1/2014 | Causey et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0121633 A1 | 5/2014 | Causey et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0174223 A1 | 6/2014 | Gross et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |
| 2015/0119798 A1 | 4/2015 | Gross et al. |
| 2015/0374926 A1 | 12/2015 | Gross et al. |
| 2016/0030665 A1 | 2/2016 | Cabiri |
| 2016/0296716 A1 | 10/2016 | Cabiri et al. |
| 2016/0346478 A1 | 12/2016 | Bar-El et al. |

FOREIGN PATENT DOCUMENTS

| | | | |
|---|---|---|---|
| CN | 1863566 A | 11/2006 | |
| CN | 101090749 A | 12/2007 | |
| CN | 101227943 A | 7/2008 | |
| CN | 101448536 A | 6/2009 | |
| CN | 101522235 A | 9/2009 | |
| CN | 101541362 A | 9/2009 | |
| CN | 201692438 U | 1/2011 | |
| CN | 201941304 U | 8/2011 | |
| CN | 102186733 A | 9/2011 | |
| CN | 102378638 A | 3/2012 | |
| DE | 1064693 B | 9/1959 | |
| DE | 19717107 A1 | 11/1998 | |
| EP | 0017412 A1 | 10/1980 | |
| EP | 0222656 A1 | 5/1987 | |
| EP | 0401179 A1 | 12/1990 | |
| EP | 1003581 B1 | 11/2000 | |
| EP | 1219312 A2 | 7/2002 | |
| EP | 1530979 A1 | 5/2005 | |
| EP | 1666080 A1 | 6/2006 | |
| EP | 2060606 A1 | 5/2009 | |
| EP | 2498589 A1 | 9/2012 | |
| FR | 2770136 A1 | 4/1999 | |
| JP | H07-194701 A | 8/1995 | |
| JP | H09-505758 A | 6/1997 | |
| JP | 2001-512992 A | 8/2001 | |
| JP | 2002-505601 A | 2/2002 | |
| JP | 2002-507459 A | 3/2002 | |
| JP | 2002-528676 A | 9/2002 | |
| JP | 2003-501157 A | 1/2003 | |
| JP | 2003-527138 A | 9/2003 | |
| JP | 2003-534061 A | 11/2003 | |
| JP | 2004-501721 A | 1/2004 | |
| JP | 2004-512100 A | 4/2004 | |
| JP | 2005-523127 A | 8/2005 | |
| JP | 2005-270629 A | 10/2005 | |
| JP | 2007-509661 A | 4/2007 | |
| JP | 2008-534131 A | 8/2008 | |
| JP | 2008-220961 A | 9/2008 | |
| JP | 2009-502273 A | 1/2009 | |
| WO | 9009202 A1 | 8/1990 | |
| WO | 9307922 A1 | 4/1993 | |
| WO | 9407553 A1 | 4/1994 | |
| WO | 9513838 A1 | 5/1995 | |
| WO | 9609083 A1 | 3/1996 | |
| WO | 9632975 A1 | 10/1996 | |
| WO | 9700091 A1 | 1/1997 | |
| WO | 9710012 A1 | 3/1997 | |
| WO | 9733638 A1 | 9/1997 | |
| WO | 9857683 A1 | 12/1998 | |
| WO | 9929151 A1 | 6/1999 | |
| WO | 9959665 A1 | 11/1999 | |
| WO | 0025844 A1 | 5/2000 | |
| WO | 200130421 A2 | 5/2001 | |
| WO | 200172357 A2 | 10/2001 | |
| WO | 0187384 A1 | 11/2001 | |
| WO | 0189607 A2 | 11/2001 | |
| WO | 0189613 A1 | 11/2001 | |
| WO | 0202165 A2 | 1/2002 | |
| WO | 0234315 A1 | 5/2002 | |
| WO | 200238204 A2 | 5/2002 | |
| WO | 0272182 A1 | 9/2002 | |
| WO | 03090833 A1 | 11/2003 | |
| WO | 04000397 A1 | 12/2003 | |
| WO | 2004032990 A2 | 4/2004 | |
| WO | 2004105841 A1 | 12/2004 | |
| WO | 2005018703 A2 | 3/2005 | |
| WO | 2005037350 A2 | 4/2005 | |
| WO | 2005072795 A2 | 8/2005 | |
| WO | 2006037434 A1 | 4/2006 | |
| WO | 06069380 A1 | 6/2006 | |
| WO | 2006102676 A1 | 9/2006 | |
| WO | 2006104806 A2 | 10/2006 | |
| WO | 2006121921 A2 | 11/2006 | |
| WO | 2007017052 A1 | 2/2007 | |
| WO | 2007051563 A1 | 5/2007 | |
| WO | 2007056504 A1 | 5/2007 | |
| WO | 2008001377 A2 | 1/2008 | |
| WO | 2008014908 A1 | 2/2008 | |
| WO | 2008057976 A2 | 5/2008 | |
| WO | 2008072229 A2 | 6/2008 | |
| WO | 2008076459 A1 | 6/2008 | |
| WO | 2008078318 A2 | 7/2008 | |
| WO | 2009044401 | 4/2009 | |
| WO | 2009046989 A2 | 4/2009 | |
| WO | 2009125398 A2 | 10/2009 | |
| WO | 2009144085 A2 | 12/2009 | |
| WO | 2010078227 A1 | 7/2010 | |
| WO | 2010078242 A1 | 7/2010 | |
| WO | 2010089313 A1 | 8/2010 | |
| WO | 2011075105 A1 | 6/2011 | |
| WO | 2011090955 A1 | 7/2011 | |
| WO | 2011090956 A2 | 7/2011 | |
| WO | 2011156373 A1 | 12/2011 | |
| WO | 2012032411 A2 | 3/2012 | |
| WO | 2012040528 A1 | 3/2012 | |
| WO | 2012160157 A1 | 11/2012 | |
| WO | 2014179774 A1 | 11/2014 | |
| WO | 2015114158 A1 | 8/2015 | |

OTHER PUBLICATIONS

U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
Office Action dated Sep. 30, 2015 in U.S. Appl. No. 13/667,739 by Cabiri.
Office Action dated Sep. 18, 2015 in U.S. Appl. No. 13/874,085 by Cabiri.
Partial European Search Report dated Nov. 24, 2015 in EP Application No. 14166592.7.
Office Action dated Dec. 1, 2015 in CN Application No. 201410289204.1.
Office Action dated Nov. 4, 2013 in EP Application No. 11 709 234.6.
Office Action dated Dec. 17, 2013 in JP Application No. 2012-529808.
Office Action dated Dec. 10, 2013 in CN Application No. 201180006567.4.
Office Action dated Jan. 8, 2014 in U.S. Appl. No. 13/521,167 by Cabiri.

(56) References Cited

OTHER PUBLICATIONS

U.S. Appl. No. 29/479,307 by Norton, filed Jan. 14, 2014.
U.S. Appl. No. 14/193,692 by Gross, filed Feb. 28, 2014.
Office Action dated Feb. 4, 2014 in EP Application No. 11 707 942.6.
English translation of an Office Action dated Mar. 5, 2014 in CN Application No. 200880117084.X.
Int'l Search Report and Written Opinion dated Apr. 3, 2014 in Int'l Application No. PCT/US2013/078040.
Extended European Search Report dated Mar. 27, 2014 in EP Application No. 14154717.4.
Office Action dated Feb. 28, 2014 in CN Application No. 201180006571.0.
U.S. Appl. No. 14/258,661 by Cabiri, filed Apr. 22, 2014.
Int'l Search Report and Written Opinion dated Jan. 7, 2014 in Int'l Application No. PCT/US2013/065211.
Office Action dated May 23, 2014 in U.S. Appl. No. 13/472,112 by Cabiri.
Office Action dated Jun. 3, 2014 in JP Application No. 2010-527595.
Office Action dated Jul. 7, 2014 in U.S. Appl. No. 12/244,666 by Gross.
Int'l Search Report and Written Opinion dated Jul. 31, 2014 in Int'l Application No. PCT/US2014/033598.
Extended European Search Report dated Aug. 7, 2014 in EP Application No. 1417477.4.
Office Action dated Aug. 6, 2014 in EP Application No. 11 707 942.6.
Office Action dated Sep. 2, 2014 in JP Application No. 2012-550069.
Office Action dated Sep. 2, 2014 in JP Application No. 2012-550068.
Office Action dated Aug. 26, 2014 in CN Application No. 201180006567.4.
Int'l Preliminary Report on Patentability dated Oct. 9, 2014 in Int'l Application No. PCT/US2013/033118.
Office Action dated Oct. 9, 2014 in U.S. Appl. No. 13/873,335.
Office Action dated Nov. 5, 2014 in U.S. Appl. No. 13/643,470 by Alon.
U.S. Appl. No. 14/553,399 by Cabiri, filed Nov. 25, 2014.
Office Action dated Nov. 2, 2014 in CN Application No. 201180006571.0.
Office Action dated Nov. 21, 2014 in U.S. Appl. No. 13/472,112 by Cabiri.
Office Action dated Nov. 21, 2014 in U.S. Appl. No. 13/429,840 by Cabiri.
Int'l Preliminary Report on Patentability dated Nov. 27, 2014 in Int'l Application No. PCT/US2013/039465.
U.S. Appl. No. 14/593,051 by Gross, filed Jan. 9, 2015.
U.S. Appl. No. 14/683,193 by Cabiri, filed Apr. 10, 2015.
Office Action dated Feb. 20, 2015 in U.S. Appl. No. 13/521,181 by Cabiri.
Office Action dated Feb. 24, 2015 in U.S. Appl. No. 14/258,661 by Cabiri.
U.S. Appl. No. 14/638,525 by Filman, filed Mar. 4, 2015.
Extended European Search Report dated Feb. 23, 2015 in EP Application No. 14166596.8.
Office Action dated Mar. 10, 2015 in U.S. Appl. No. 13/643,470 by Alon.
Office Action dated Mar. 10, 2015 in U.S. Appl. No. 12/244,666 by Gross.
Extended European Search Report dated Feb. 23, 2015 in EP Application No. 14166591.9.
Office Action dated Mar. 10, 2015 in CN Application No. 201180006567.4.
Office Action dated Mar. 31, 2015 in JP Application No. 2012-550068.
Webpage description of Daikyo Crystal Zenith® polymer, Manufactured by Daikyo Seiko, Ltd. (Jan. 6, 2009).
Webpage description of Copaxone®, Manufactured by Teva Pharmaceutical Industries Ltd. . (Jan. 6, 2009).
Int'l Preliminary Report on Patentability dated May 14, 2015 in Int'l Application No. PCT/US2013/065211.
Office Action dated May 7, 2015 in JP Application No. 2012-550069.
Office Action dated May 13, 2015 in CN Application No. 201380025566.3.
U.S. Appl. No. 14/715,791 by Cabiri, filed May 19, 2015.
Office Action dated May 1, 2015 in U.S. Appl. No. 14/638,525 by Filman.
Office Action dated Jun. 4, 2015 in U.S. Appl. No. 13/667,739 by Cabiri.
Int'l Search Report and Written Opinion dated Jul. 6, 2017 in Int'l Application No. PCT/US2017/022966.
Daikyo Crystal Zenith® polymer, Manufactured by Daikyo Seiko, Ltd. (Jun. 25, 2008).
Copaxone®, Manufactured by Teva Pharmaceutical Industries Ltd. (2009).
Int'l Search Report dated May 13, 2009 in Int'l Application No. PCT/IL2008/001312.
Int'l Preliminary Report on Patentability dated Apr. 7, 2010 in Int'l Application No. PCT/IL2008/001312; Written Opinion.
Int'l Search Report dated Apr. 26, 2010 in Int'l Application No. PCT/US2009/069552.
Office Action dated Apr. 5, 2010 in U.S. Appl. No. 12/244,666.
Office Action dated Sep. 21, 2010 in U.S. Appl. No. 12/244,666.
Office Action dated Apr. 5, 2010 in U.S. Appl. No. 12/244,688.
Office Action dated Sep. 2, 2010 in U.S. Appl. No. 12/244,688.
Office Action dated Sep. 30, 2010 in U.S. Appl. No. 12/689,250.
Int'l Search Report dated Jan. 12, 2011 in Int'l Application No. PCT/US2010/048556; Written Opinion.
U.S. Appl. No. 60/997,459, filed Oct. 2, 2007.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
International Preliminary Report on Patentability dated on Jul. 5, 2011 in International Application No. PCT/US2009/069552; Written Opinion.
Office Action dated Jul. 13, 2011 in U.S. Appl. No. 12/559,563.
Int'l Preliminary Report on Patentability dated Sep. 1, 2011 in Int'l Application No. PCT/US2010/048556.
Office Action dated Sep. 6, 2011 in U.S. Appl. No. 12/345,818.
Office Action dated Feb. 21, 2012 in U.S. Appl. No. 12/689,249.
Int'l Search Report dated Jun. 17, 2011 in Int'l Application No. PCT/US2011/021604.
Int'l Search Report dated Oct. 12, 2011 in Int'l Application No. PCT/US2011/021605.
Office Action dated Oct. 28, 2011 in U.S. Appl. No. 12/615,828.
Int'l Search Report dated Sep. 22, 2011 in Int'l Application No. PCT/IL11/00368; Written Opinion.
U.S. Appl. No. 13/521,181 by Cabiri, filed Jul. 9, 2012.
U.S. Appl. No. 13/521,167 by Cabiri, filed Jul. 9, 2012.
Office Action dated May 16, 2012 in U.S. Appl. No. 12/615,828.
Office Action dated Jul. 2, 2012 in U.S. Appl. No. 13/272,555.
Office Action dated May 3, 2012 in CN Application No. 200880117084.X.
U.S. Appl. No. 13/472,112 by Cabiri, filed May 15, 2012.
U.S. Appl. No. 13/429,840 by Cabiri, filed Mar. 26, 2012.
Int'l Preliminary Report on Patentability dated Aug. 2, 2012 in Int'l Application No. PCT/US2011/021604.
U.S. Appl. No. 13/643,470 by Alon, filed Oct. 25, 2012.
U.S. Appl. No. 13/733,516 by Cabiri, filed Jan. 3, 2013.
Office Action dated Jan. 8, 2013 in JP Application No. 2010-527595.
Int'l Preliminary Report on Patentability dated Feb. 7, 2013 in Int'l Application No. PCT/US2011/021604.
Int'l Preliminary Report on Patentability dated Feb. 7, 2013 in Int'l Application No. PCT/US2011/021605.
English translation of an Office Action dated Jan. 30, 2013 in CN Application No. 200880117084.X.
U.S. Appl. No. 13/873,335 by Filman, filed Apr. 30, 2013.
U.S. Appl. No. 13/892,905 by Cabiri, filed May 13, 2013.
U.S. Appl. No. 13/874,121 by Degtiar, filed Apr. 30, 2013.

(56) References Cited

OTHER PUBLICATIONS

U.S. Appl. No. 13/874,085 by Cabiri, filed Apr. 30, 2013.
U.S. Appl. No. 13/874,017 by Cabiri, filed Apr. 30, 2013.
Int'l Search Report and Written Opinion dated Jul. 26, 2013 in Int'l Application No. PCT/US2012/039465.
Int'l Search Report and Written Opinion dated Aug. 5, 2013 in Int'l Application No. PCT/US2013/033118.
U.S. Appl. No. 13/964,651 by Gross, filed Aug. 12, 2013.
Office Action dated Aug. 15, 2013 in CN Application No. 200880117084.X.
Office Action dated Oct. 9, 2013 in IL Application No. 208634.
Office Action dated Nov. 5, 2013 in JP Application No. 2010-527595.
Office Action dated Sep. 29, 2013 in CN Application No. 201080040968.7.
Office Action dated Jul. 31, 2015 in U.S. Appl. No. 13/521,181 by Cabiri.
Office Action dated Aug. 13, 2015 in U.S. Appl. No. 14/553,399 by Cabiri.
Int'l Preliminary Report on Patentability dated Jul. 16, 2015 in Int'l Application No. PCT/US2013/078040.
Notice of Allowance dated Aug. 24, 2015 in U.S. Appl. No. 29/479,307 by Norton.
West Introduces the Daikyo Crystal Zenith RU Prefillable Syringe, Pharmaceutical Online, Jun. 2008, downloaded from webpage: http://www.pharmaceuticalonline.com/article.mvc/west-introduces-prefillable-syringe-system, Download date: Jan. 2009, original posting date: Jun. 2008, 2 pages.
Office Action dated May 25, 2016 in U.S. Appl. No. 14/874,017 by Cabiri.
Extended European Search Report dated Feb. 13, 2017 in EP Application No. 16171626.1.
Extended European Search Report dated Mar. 8, 2016 in EP Application No. 14166592.7.
Extended European Search Report dated Jul. 31, 2017 in EP Application No. 16190054.3.

* cited by examiner

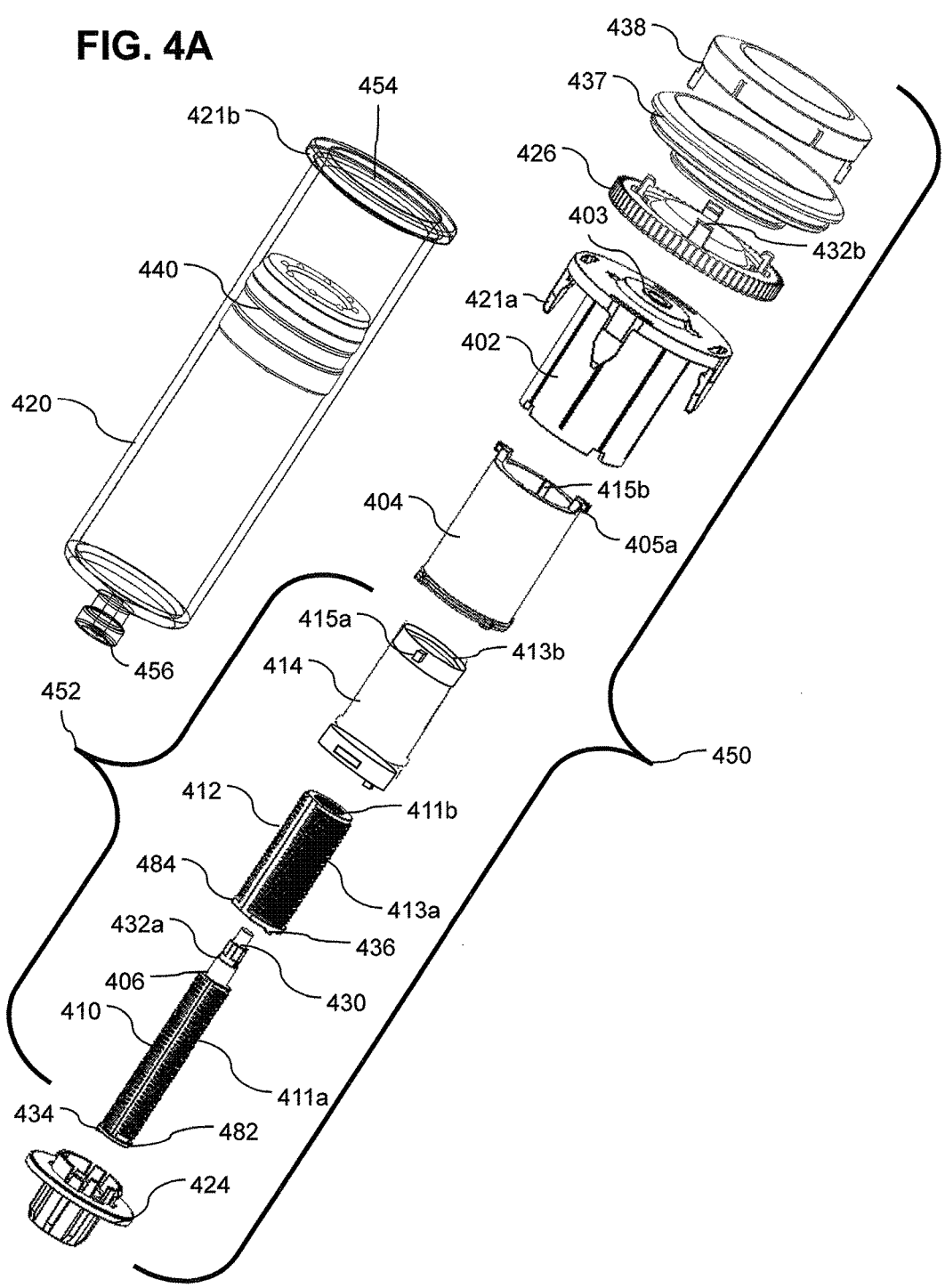

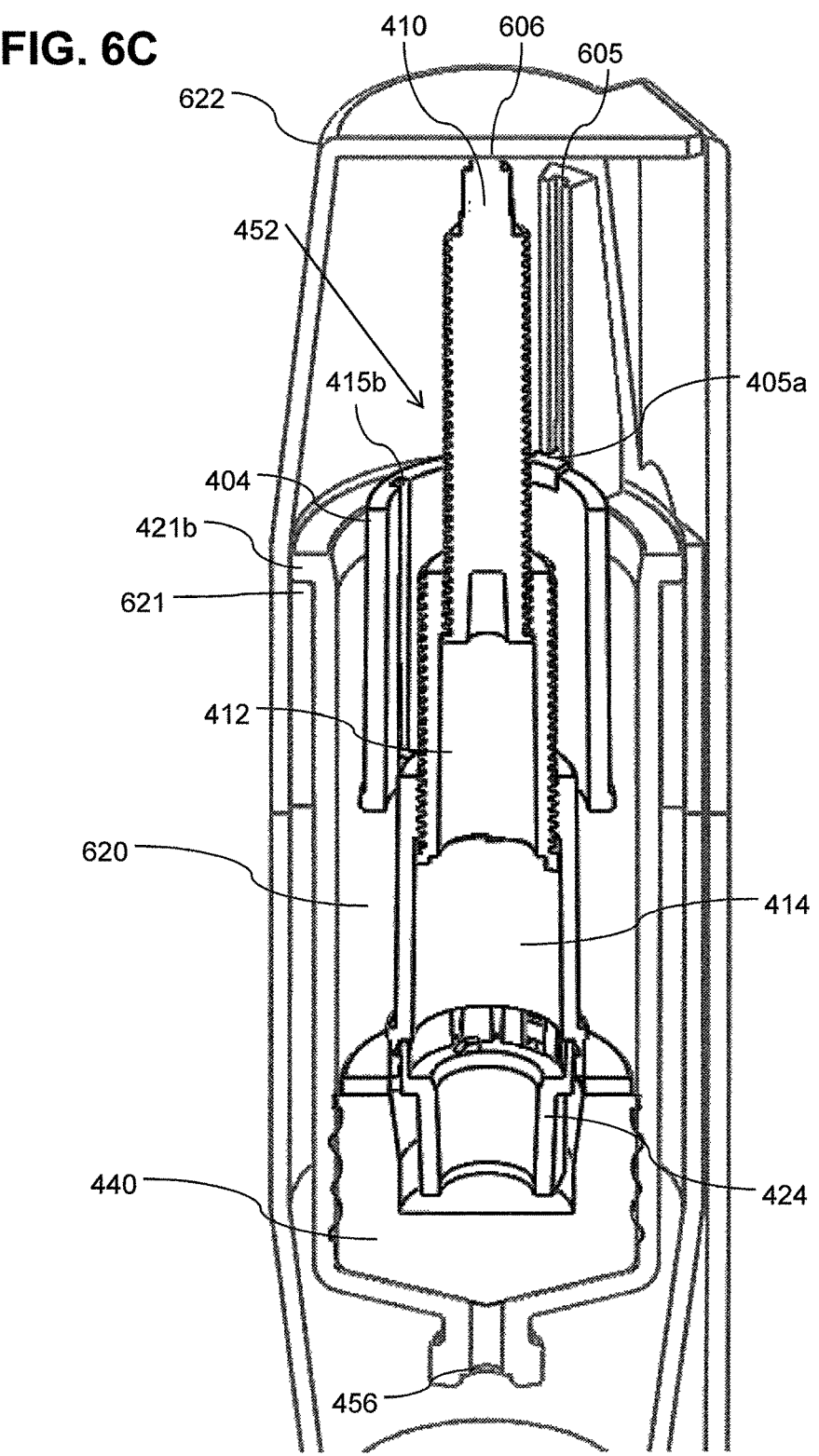

LINEAR ROTATION STABILIZER FOR A TELESCOPING SYRINGE STOPPER DRIVERDRIVING ASSEMBLY

BACKGROUND OF THE INVENTION

The present invention, in some embodiments thereof, relates to a stopper driver for a drug delivery device and, more particularly, but not exclusively, to a telescoping stopper driver of a drug cartridge.

U.S. Pat. No. 6,800,071 discloses, "an improved pump, reservoir and reservoir piston for," "controlled delivery of fluids. A motor is operably coupled to a drive member, such as a drive screw, which is adapted to advance a plunger slide in response to operation of the motor. The plunger slide is removably coupled to the piston. The piston comprises a first member and a second member. The first member has an external proximate side and an external distal side. The external proximate side is adapted to contact the fluid and is made of a material having a first stiffness. The second member has a first side and a second side and is at least partially disposed within the first member. The first side of the second member is adjacent to the external proximate side of the first member and is made of a material having a stiffness which is greater than the first stiffness."

International Patent Application Publication No. WO/2011/090956 by the instant applicant (Cabiri) and/or U.S. Patent Application Publication No. 2009/0093792 to Gross.

Additional background art includes U.S. Patent Application Publication 20130304021, U.S. Patent Application Publication 20130296799, U.S. Patent Application Publication 20130245596, U.S. Pat. No. 8,465,455, International Patent Application Publication No. WO/2011/090956 and U.S. Patent Application Publication No. 2009/0093792.

BRIEF SUMMARY OF THE INVENTION

According to an aspect of some embodiments of the invention, there is provided an assembly for driving a stopper in a drug reservoir of a drug delivery device comprising: a telescoping assembly that telescopes by relative rotation between at least a proximal shaft and a distal shaft oriented along and axis of the reservoir; the distal shaft configured to engage the stopper of the drug reservoir; an anti-rotational guide sized to move along the axis of the reservoir; the anti-rotational guide slidably and anti-rotationally coupled to a housing of the drug delivery device; a coupling slidably and anti-rotationally linking the anti-rotational guide to the distal shaft; the sliding and anti-rotation with respect to the axis of the reservoir such that rotating the proximal shaft with respect to the anti-rotational guide moves the distal shaft along the axis and moves the distal shaft with respect to the anti-rotational guide the anti-rotational guide also moving along the axis.

According to some embodiments of the invention, a maximum axial movement of the distal shaft with respect to the reservoir is greater than a maximum axial movement of the guide with respect to the reservoir.

According to some embodiments of the invention, the assembly further comprises: an intermediate shaft threadably engaged to the proximal shaft and to the distal shaft such that the telescoping assembly also telescopes by rotating the proximal shaft with respect to the intermediate shaft.

According to some embodiments of the invention, a maximum axial movement of the distal shaft with respect to the reservoir is greater than a maximum axial movement of the intermediate shaft with respect to the reservoir.

According to some embodiments of the invention, the assembly further comprises: a linear stabilizer coupled to the proximal shaft, inhibiting axial movement of the proximal shaft in a proximal direction with respect to the linear stabilizer, the linear stabilizer coupled to the reservoir inhibiting axial movement of the linear stabilizer in a proximal direction with respect to the reservoir, such that the rotation of the proximal shaft causes the distal shaft to advance distally inside of the drug reservoir.

According to some embodiments of the invention, the linear stabilizer includes a connector shaped to attach to a proximal portion of the reservoir.

According to some embodiments of the invention, the connector is shaped to attach to a flange of the reservoir.

According to some embodiments of the invention, the linear stabilizer includes an anti-rotational connector fitting to the housing for preventing rotation of the linear stabilizer with respect to the housing and wherein the anti-rotational guide slidably engages to the housing by means of the linear stabilizer.

According to some embodiments of the invention, the reservoir and the assembly form a cartridge and wherein the housing includes an opening fitting the cartridge and wherein the anti-rotational connector is shaped to connect to the housing to limit rotation of the anti-rotational connector with respect to the housing when the cartridge is inserted into the opening.

According to some embodiments of the invention, the assembly further comprises: a bearing preventing proximal movement of the proximal shaft with respect to the housing and allowing rotation of the proximal shaft with respect to the housing.

According to some embodiments of the invention, the assembly further comprises a stopper interface for driving the stopper; the interface is optionally connected to the distal shaft.

According to some embodiments of the invention, the coupling includes a protrusion slidably inserted into a track.

According to an aspect of some embodiments of the invention, there is provided a method of supplying a drug to a delivery device comprising: providing a reservoir containing a drug and sealed with a stopper and a telescoping assembly that telescopes by rotating a proximal shaft with respect to a distal shaft; the distal shaft configured to engage the stopper; slidably and anti-rotationally engaging an anti-rotational guide to a housing of the delivery device; preventing rotation of the distal shaft with respect to the housing by slidably guiding the distal shaft along the anti-rotational guide, and extending the distal shaft and the anti-rotational guide linearly inside a cavity of the reservoir toward a distal end of the reservoir by rotating the proximal shaft wherein a distance of the extending of the distal shaft is greater than a distance of the extending of the anti-rotational guide.

According to some embodiments of the invention, the method further includes: driving the rotating of the proximal shaft with a motor of the drug delivery device.

According to some embodiments of the invention, the distal shaft is initially distanced proximally from the stopper and the extending is toward the stopper.

According to some embodiments of the invention, the distal shaft abuts against the stopper and further comprising driving the stopper inside the cavity toward the distal end of the reservoir by the extending of the distal shaft.

According to some embodiments of the invention, the method further comprises: attaching a linear stabilizer to the reservoir and inhibiting proximal movement of the proximal shaft with respect to the linear stabilizer.

According to some embodiments of the invention, the method further comprises: forming a cartridge including the reservoir, the stopper, the distal shaft, the anti-rotational guide, and the linear stabilizer and inserting the cartridge as a single unit into the drug delivery device.

According to some embodiments of the invention, the method further comprises: coupling the housing to the proximal shaft and inhibiting proximal movement of the proximal shaft with respect to the housing.

According to some embodiments of the invention, the preventing includes inserting a protrusion into a track.

According to some embodiments of the invention, the inserting includes elastically deforming at least one of the distal shaft and the anti-rotational guide.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 4A is an exploded view of a reservoir and a stopper driver including sliding sleeve anti-rotational guides in accordance with an embodiment of the present invention;

FIG. 6C is a cross sectional view of a reservoir and a stopper driver stabilized by a device housing in a retracted configuration in accordance with an embodiment of the present invention.

DETAILED DESCRIPTION OF THE INVENTION

Figure 1A:
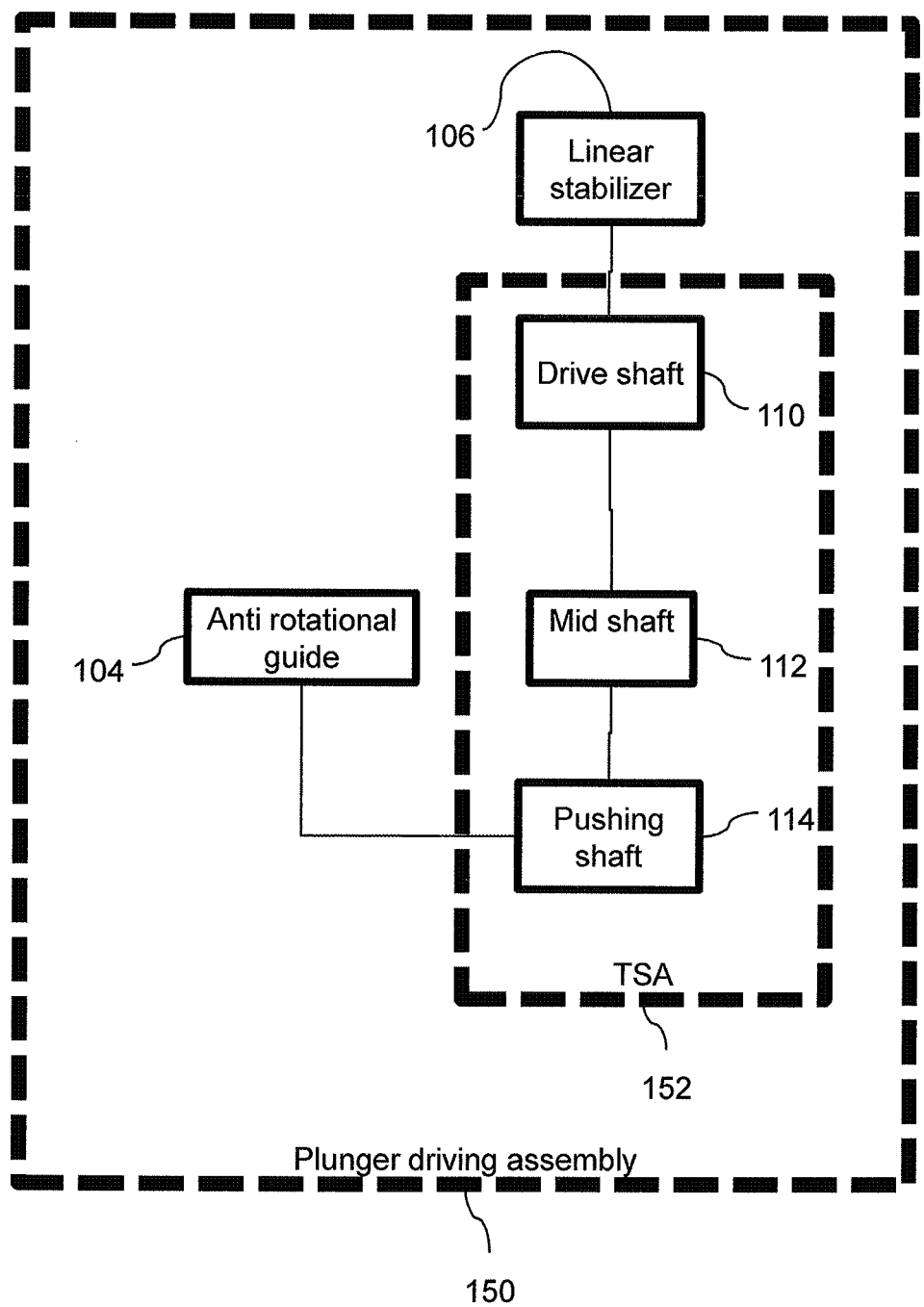
FIG. 1A is a block diagram of a stopper driver in accordance with an embodiment of the present invention.

The present invention, in some embodiments thereof, relates to a stopper driver for a drug delivery device and, more particularly, but not exclusively, to a telescoping stopper driver of a drug cartridge.

Overview

An aspect of some embodiments of the present invention relates to an anti-rotational guide for stopper driving assembly of a drug delivery device. Optionally, a distal shaft of the driver assembly is held rotationally stationary by the guide while being driven distally into the reservoir by relative rotation of a rotating proximal element. As the distal element progresses distally into the reservoir, the shaft may slide distally with respect to the guide. Additionally or alternatively, the guide and shaft may slide together distally into the reservoir. In some embodiment, the proximal element and the distal shaft may telescope when rotated in relation to one another. The proximal element may be held axially immobile with respect to the reservoir such that the telescoping of the proximal and distal elements forces the distal shaft into the reservoir.

Some embodiments may include a linear and/or a rotational stabilizer. For example a rotational stabilizer may be supported by a housing of the drug delivery device and/or a motor mount such that torque on the telescoping assembly is balanced against the anti-rotational guide and/or the motor and/or the housing of the delivery device. Optionally the torque will not be applied to the drug reservoir and/or the stopper and/or any part that is in contact with the drug.

In some embodiments, a linear force between the stopper and the driver assembly is balanced against the reservoir. Optionally the linear stress between the pushing assembly and the stopper is balanced with negligible or no external linear stresses on the drug delivery device and/or between the reservoir and the drug delivery device.

In some embodiments, the driver assembly may be attached to a drug reservoir to form a cartridge. The entire cartridge is optionally inserted as a unit into the drug delivery device. In some embodiments, the cartridge may meter out a drug while producing negligible or no external axial forces on the drug delivery device. For example, the cartridge assembly may include a linear stabilizer connecting the TSA to the drug reservoir. For example, the linear stabilizer may connect to the reservoir near a proximal opening of the reservoir and/or on a proximal flange thereof. Optionally, linear forces between a stopper and the TSA may be balanced by forces between the linear stabilizer and the reservoir. Optionally, the entire cartridge assembly is inserted into a proximal opening in a drug delivery device. Optionally when the cartridge is inserted into the proximal opening of the drug delivery device, a cannula pierces a septum creating a fluid path between the reservoir and the drug delivery device. For example the septum may be located on and/or near the distal end of the cartridge. Alternatively or additionally example the septum may be located on and/or near the distal portion of the drug delivery device.

In some embodiments a cartridge pushing assembly may be attached to a proximal opening of a reservoir without regard to the precise longitudinal position of a stopper in the reservoir. Optionally, after connecting the stopper pushing assembly to the reservoir, the TSA may be extended until the pushing assembly contacts the stopper. For example, the TSA may be extended before inserting the cartridge assembly into a drug device. Alternatively or additionally, The TSA may be extended after inserting the cartridge assembly into the drug delivery device.

In some embodiments, the stroke length of the TSA may be greater than the minimum length of the TSA. For example a TSA may have three telescoping shafts and/or three telescoping guides. For example a telescoping shaft may include an extension rod. Alternatively or additionally a TSA may have four telescoping shafts and/or four telescoping guides. Alternatively or additionally a TSA may have five telescoping shafts and/or five telescoping guides. For example a TSA may have a contracted configuration with length ranging between 0.8 and 1.6 cm and/or an extended configuration with length ranging between 2.0 to 4.0 cm. Optionally, the extended length of the TSA may range between 2.0 to 3.0 times the contracted length and/or between 3.0 to 5.0 times the contracted length.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Cartridge Assembly

Referring now to the drawings, FIG. 1A is a block diagram of a stopper driving assembly 150 in accordance with an embodiment of the present invention. Driving assembly 150 optionally includes a linear stabilizer 106 supporting a driver assembly 150 and/or balancing linear forces between driver assembly 150 and a stopper (for example stopper 140 of FIG. 1B). Driver assembly 150 optionally includes an anti-rotational guide, for example guide 104. Anti-rotational guide 104 optionally supports the driver assembly and/or balances torque between the driver assembly and a motor (for example motor 108 of FIG. 1B).

In some embodiments, stopper driver assembly 150 may include a telescoping assembly (for example TSA 152). Optionally, TSA 152 includes a proximal shaft, for example a threaded drive shaft 110 and/or a threaded mid shaft 112 and/or a distal shaft, for example a threaded pushing shaft 114. Shafts 110, 112 and/or 114 may be coupled such that rotating drive shaft 110 with respect to pushing shaft 114 causes TSA 152 to lengthen and/or shorten. Optionally axial movement of drive shaft 110 is limited by linear stabilizer 106 such that rotating drive shaft 110 with respect to pushing shaft 114 causes pushing shaft 114 to move linearly with respect to linear stabilizer 106. Optionally, a coupling links pushing shaft 114 to anti-rotational guide 104. For example, rotation of pushing shaft 114 may be limited by anti-rotational guide 104 such that rotating drive shaft 110 with respect to anti-rotational guide 104 causes TSA 152 to lengthen and/or shorten. Alternatively or additionally, drive shaft 110 and/or pushing shaft 114 may be replaced by a nut and/or threaded disk and/or ring.

Figure 1B:
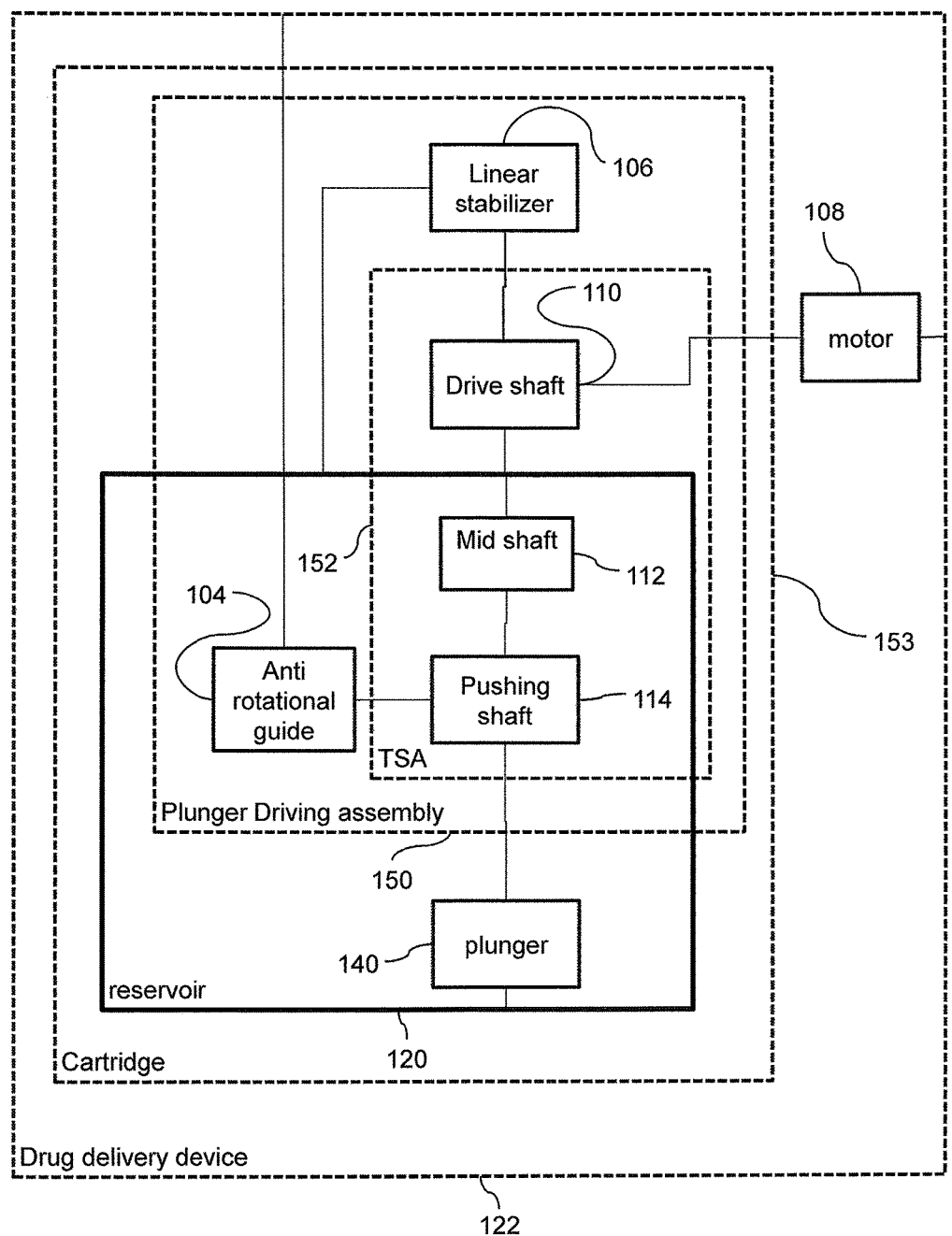
FIG. 1B is a block diagrams of a cartridge inserted into a drug delivery device in accordance with an embodiment of the present invention.

FIG. 1B is a block diagram of a cartridge 153 inserted into a drug delivery device 122 in accordance with an embodiments of the present invention. Optionally, cartridge 153 includes driving assembly 150, a drug reservoir 120 and/or a stopper 140. Optionally drug delivery device 122 includes a motor 108. Alternatively or additionally motor 108 may include a DC electric motor, a chemical engine, a brushless motor, and AC motor, an actuator etc.

In some embodiments, linear stabilizer 106 may be attached to drug reservoir 120 and/or pushing shaft 114 may abut against stopper 140 such that extending TSA 152 moves stopper 140 axially with respect to reservoir 120. Axial back forces of stopper 140 with respect to reservoir 120 (for example due to friction between stopper and reservoir and/or due to flow resistance) are optionally balanced within cartridge 153 by a linear force between linear stabilizer 106 and reservoir 120.

In some embodiments, motor 108 may apply a torque to drive shaft 110. Optionally, anti-rotational guide 104 may be attached to drug reservoir 120 such that activating motor 108 moves pushing shaft 114 axially with respect to drive shaft 110. Friction between driving shaft 110 and pushing shaft 114 are optionally balanced by an anti-torque between motor 108 and anti-rotational guide 104 such that TSA 152 acts as a linear actuator putting a net linear force (and/or a negligible torque) on the parts of the device that are in contact with the drug (for example stopper 140 and/or reservoir 120).

In some embodiments, any or all of linear stabilizer 106, drive shaft 110, mid shaft 112, pushing shaft 114 and/or anti-rotational guide 104 may be partially and/or wholly located inside reservoir 120. Alternatively or additionally, any or all of linear stabilizer 106, drive shaft 110, mid shaft 112, pushing shaft 114 and/or anti-rotational guide 104 may be wholly or partially located outside reservoir 120 when TSA 152 is contracted and/or may move wholly or partially into reservoir 120 when TSA 152 expands.

In some embodiments, mid-shaft 112 and/or anti-rotational guide 104 may move axially. For example mid-shaft 112 and/or anti-rotational guide 104 may move into and/or out of reservoir 120. Optionally mid-shaft 112 may float. In the current disclosure, in some configurations (for example when TSA 152 is partially extended) the position of a floating part may be indeterminate. For example the part may move without changing the length of TSA 152. For example the order of movement of parts of TSA 152 may be not fixed. Optionally, driver shaft 110 may be an inner shaft and the pushing shaft 114 may be an outer shaft. Alternatively or additionally driver shaft 110 may be an outer shaft and the pushing shaft 114 may be an inner shaft. Any or all of the components of the current invention may be made of plastic and/or metal and/or another material.

Driving a Stopper

Figure 2:
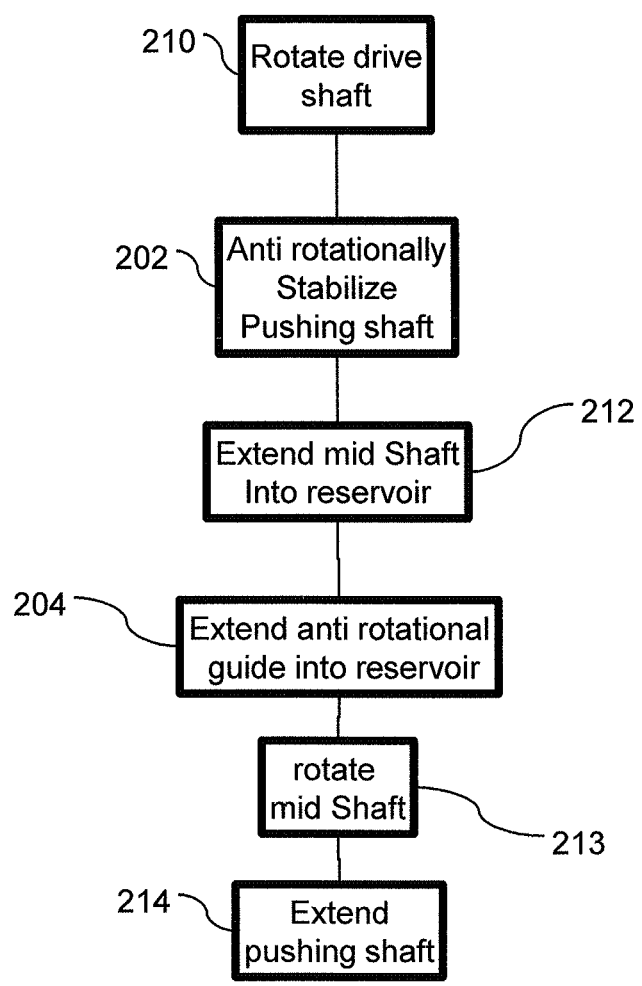
FIG. 2 is a flow chart illustrating a method of driving a stopper in accordance with an embodiment of the present invention.

FIG. 2 is a flow chart illustrating a method of driving a stopper in accordance with an embodiment of the present invention. In some embodiments, a TSA may be extended or retracted by more than 100% its minimum length by rotating 210 a single shaft and/or by inhibiting rotation of a single shaft. For example, a TSA may be opened by rotating 210 a drive shaft. Optionally a proximal drive shaft may be located proximally to a distal pushing shaft. For example, the drive shaft may be rotated 210 with respect to a drug delivery device by a motor mounted on the device. For example rotation 210 of the drive shaft may be with respect to the housing of the drug delivery device and/or with respect to a mount of the motor. Optionally, while the drive shaft is rotating, a pushing shaft may be inhibited 202 from rotating. For example, an anti-rotational guide may prevent the pushing shaft from rotating with respect to the drug delivery device housing and/or with respect to the motor and/or with respect to a motor mount. Rotating 210 the drive shaft with respect to the pushing shaft optionally extends the TSA and/or the pushing shaft and/or a stopper.

In some embodiments, the mid shaft may axially float. For example, when the TSA is extended the mid shaft may either extend linearly 212 with the pushing shaft and/or rotate 213 with the drive shaft. Optionally, for some lengths of the TSA, the position of the mid shaft may be indeterminate. For example, rotating 210 the drive shaft may, for example, extend 212 a mid-shaft into a reservoir (for example when the drive shaft rotates faster than the mid-shaft and/or by means of threading coupling the drive shaft to the mid shaft). Optionally, extending 212 the mid-shaft into the reservoir simultaneously extends 214 the pushing shaft into the reservoir. Alternatively or additionally, rotating 210 the drive shaft may rotate 213 the mid-shaft. Optionally, rotating 213 the mid-shaft extends 214 a pushing shaft into the reservoir (for example by means of threading coupling the drive shaft to the mid shaft). Rotation and/or extension of the mid shaft may occur concurrently and/or sequentially.

In some embodiments, the anti-rotational guide may axially float. For example, when the TSA is extended the anti-rotational guide may either extend 204 (for example moving axially with respect to and/or into the reservoir) along with the pushing shaft and/or the anti-rotational guide may remain stationary with respect to the reservoir and/or the pushing shaft may extend 214 axially with respect to the anti-rotational guide. Optionally, for some lengths of the TSA, the position of the anti-rotational guide may be indeterminate. In some embodiments, a pushing shaft may rotate while another element of the TSA is anti-rotationally stabilized (inhibited from rotating with respect for example to a drug delivery device housing and/or a motor).

Assembly and/or Installation of a Stopper Driver

Figure 3:
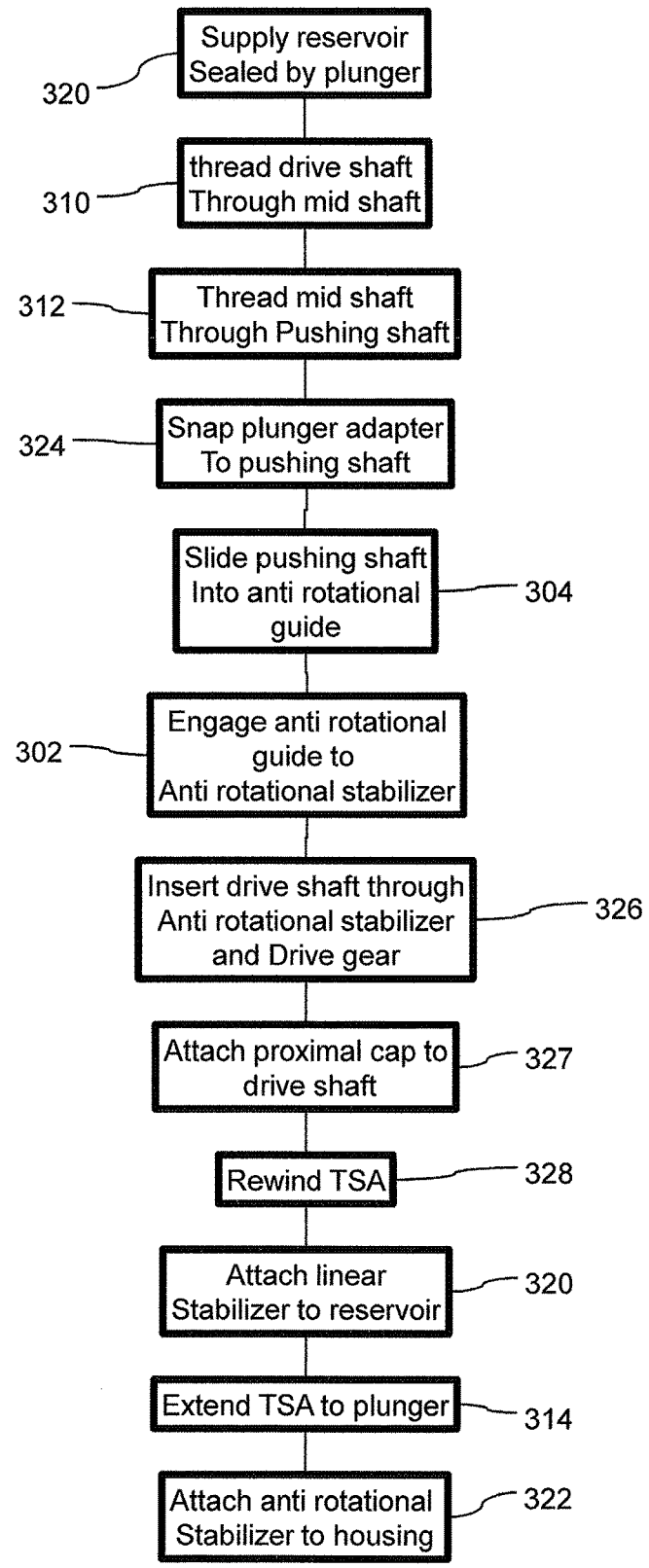
FIG. 3 is a flow chart illustrating a method of assembling a stopper driver in accordance with an embodiment of the present invention.

FIG. 3 is a flow chart illustrating a method of assembling a stopper driver in accordance with an embodiment of the present invention. For example the stopper driver, may fit a reservoir fillable with standard pharmaceutical equipment (for example in an existing clean room with filling equipment made for a standard syringe and/or cartridge). Optionally, the stopper driver engages the stopper located at an arbitrary position within the reservoir. In some embodiments the stopper driver may be assembled with snap together parts. The parts are optionally made of molded materials such as plastic, for example polyoxymethylene (POM) resin.

In some embodiments a drug reservoir is supplied 320. Optionally the reservoir may be prefilled. For example, the reservoir may be filled using standard filling equipment. For example, the reservoir may have a cylindrical and/or tubular body of arbitrary cross section. For example the body may be in the form of a right circular cylinder. The reservoir optionally includes an internal cavity. Optionally, the internal cavity may be of arbitrary shape. For example, the internal cavity may have a smooth wall over at least half its length and/or over at least 90% of its length. For example the cavity of the reservoir may be substantially a right circular cylinder over at least half its length and/or over at least 90% of its length. For example the internal cavity may be coaxial with the outer walls of the reservoir over at least half its length and/or over at least 90% of its length. For example the cross section of the cavity may be uniform over at least half its length and/or over at least 90% of its length. Optionally the reservoir may include a distal opening. For example the distal end of the reservoir may include cannula for example a hypodermic needle and/or a mount for such. Alternatively or additionally the distal end of the reservoir and/or the distal opening may include a seal, for example a septum and/or sterile cover for example a needle cover. The proximal end of the reservoir may include a proximal opening. Optionally the proximal opening may be larger than the distal opening. For example the cross sectional area of the proximal opening may range between 5 to 50 times the cross sectional area of the distal opening and/or 50 to 500 times the cross sectional area of the distal opening. Optionally the cross sectional opening may be beveled and/or may smoothly connect to the internal cavity of the reservoir. Optionally, a stopper may be inserted into the proximal opening. Optionally the stopper may seal and/or preserve sterility of the contents of the reservoir. Optionally the position of the stopper may vary dependent on the volume of the contents of the reservoir. Optionally the proximal end of the reservoir may include a flange. For example the flange may extend from the between 20% to 100% of the perimeter of the reservoir. For example the flange may extend between 1 mm and 2 cm from the internal walls of the proximal opening. Optionally the reservoir may be made as a single integral unit for example of molded glass or plastic and/or cut and/or processed tubing.

In some embodiments a TSA is assembled in a simple manner. Optionally, assembly may be unidirectional. Unidirectional assembly may include, for example, insertion of all or most shafts from the same end of the TSA. Unidirectional assembly may include, for example, threading some most and/or all shafts in the same direction. Optionally, assembly may be accomplished without reversing orientation of the parts during assembly and/or adding without other complimentary work such as welding, riveting, plastic deformation etc.

In some embodiments, a series of shafts may be threaded together. For example for a leading end of an interior shaft may be inserted through a rear (distal) end of a more exterior shaft. For example a leading end of an interior shaft may be threaded into a more exterior shaft and/or a distal end of the more exterior shaft. As used herein, the term/phrase leading end means the end of a TSA from which the inner shaft projects in the extended state. As used herein, the term/phrase rear end means the end of a TSA from which the outer shaft projects in the extended state. As used herein, the term/phrase threading means screwing the more interior shaft towards the leading direction (in some embodiments threading is used to assemble and/or extend the TSA). As used herein, the term/phrase de-threading means screwing the more interior shaft towards the rear of the outer shaft (in some embodiments dethreading is used to contract the TSA). Alternatively or additionally, in some embodiments dethreading may be used to assemble and/or extend the TSA and/or threading may be used to contract the TSA. Optionally, the leading end of the most inner shaft may include a fastener and/or the rear end of the most external shaft may include a fastener.

In some embodiments of the invention a TSA resists disengagement and/or detaching of shafts upon extension. For example, an internal shaft of the TSA may include a flange and/or a step on its rear end. The flange may prevent disengagement from a more outer shaft. Alternatively or additional the flange may be replaced by a protrusion of a different geometry.

In some embodiments, a TSA may be simple assembled unidirectionally from a reverse extended position. The assembled TSA may optionally resist dis-assembly by extension.

In some embodiments a TSA is assembled from molded parts. In some embodiments, molding provides highly precise part geometries. Molded parts may optionally be assembled with minimal modifications during assembly. For example, the assembly of the TSA may be include minimal or no adhesion of parts, and/or changing of part geometries by heat and/or ultrasonic means and/or by force (for example by crimping). The molded parts may optionally include features to facilitate proper orientation. The molded parts may optionally include built in connectors and/or fasteners (for example snaps, latches, catches, hooks, clasps and the like). In some embodiments that parts may be molded of plastic. For example plastic may include low friction materials. Examples of such materials include a Polybutylene terephthalate (PBT) resin (for example CELANEX® resin available from TICONA) and/or a POM resin (for example Delrin® resin DuPont™).

In some embodiments an internal shaft may be molded in a single piece with the rear flange and/or projections. The flange and/or projection may optionally impede unintentional disengagement of the shaft. In some embodiments a part may be molded in a single piece with a fastener. In some embodiments a part may be molded in a single piece with a thread stopper and/or an interference element.

In some embodiments, some or all of the shafts of the assembly may optionally be supplied disassembled from an end cap. For example, the some or all of the shafts and/or end caps may include fasteners. The shafts may optionally be supplied with flanges inhibiting disassembly due to overextension. For example, an internal shaft may have a flange on a rear end. The flanges and/or fasteners may optionally be intrinsic. For example, the shafts and/or caps may be molded in a single piece with the fasteners and/or flanges.

In some embodiments, some or all of the shafts may be assembled together by reverse extension. For example, a leading end of an internal shaft may be inserted into a rear end of a more external shaft. For example, the internal shaft may be threaded from a disassembled (reverse extended) position through its contracted position out the leading end of a mating shaft to an extended position. In some embodiments, flanges which prevent the shafts from disattaching in the extended state may also prevent attaching the shafts from the extended state and threading them to the contracted state.

In some embodiments, a fastener may be supplied on a leading end of an inner shaft. Once the leading end of an inner shaft extends beyond the mating shaft, an end cap (for example a driver and/or an actuator) may be fastened to the fastener. Optionally an interference element may be supplied. For example the interference element may include a flange that blocks dethreading back to the reverse extended position and/or may include one or more protrusions that prevent thread lock resulting from collision between a shaft and an end cap.

Referring now to FIG. 3, the figure illustrates an exemplary method for assembling a TSA. In some embodiments, the leading end of an inner shaft (for example drive shaft 410 illustrated of FIG. 4A) may be threaded 310 into the rear end of a mid shaft (for example mid shaft 412 of FIG. 4A). Optionally the leading end of the inner shaft may be threaded all the way through a mid shaft until the leading end of the inner shaft protrudes from the leading end of the mid shaft.

In some embodiments, the leading end of the mid shaft along with the inner shaft may be threaded 312 into a rear end of a distal outer shaft (for example pushing shaft 414 of FIG. 4A). Threading 312 may continue until the leading end of the inner shaft protrudes out the leading end of the outer shaft. Optionally, the assembly may include only two shafts and/or three shafts and/or more than three shafts (for example four, five, six or more shafts). In some embodiments, regardless of the number of shafts, the assembly of shafts may have a fastener of the inner shaft protruding from the leading end and a fastener of an outer shaft protruding from the rear end.

In some embodiments, an actuator cap (for example distal cap 424 of FIG. 4A) may be attached 324 to the fastener of the outer shaft. For example, an actuator cap may include a syringe stopper and/or a fitting to attach to a syringe stopper. Examples of syringe stoppers actuated by telescopic assemblies can be found for example in International Patent Application Publication No. WO/2011/090956 to Cabiri and/or U.S. Patent Application Publication No. 2009/0093792 to Gross which are herein incorporated in their entirety by reference.

In some embodiments, an outer shaft may be connected 304 to a first anti-rotational guide (for example anti-rotational guide 404 of FIG. 4A). For example the first guide and the outer shaft may move axially with respect to each other, but may be inhibited from rotation with respect to each other around the axis. Optionally the first guide may be connected 302 to a second guide (for example stabilizer 402 of FIG. 4A). For example the second guide and the first guide may move axially with respect to each other, but may be inhibited for rotating with respect to one another around the axis. The linear stabilizer in some embodiments is also an anti-rotational stabilizer. In some embodiments, the first anti-rotational guide and the second anti-rotational guide may be collapsed such that the proximal end of the drive shaft protrudes beyond the proximal ends of the guides. The proximal end of the drive shaft may be connected to a transmission. For example, the proximal end of drive shaft 410 may be inserted 326 through a slot in a gear (for example connector 432a of drive shaft 410 may be inserted into slot 432b of a cartridge gear 426 of FIG. 4A). Optionally, the proximal end of the assembly will be held together 327 by a proximal end cap (for example an end cap 438 may snap to a retainer 437 which may hold to a fastener 430 on the proximal end of drive shaft 410 in FIG. 4A).

In some embodiments, after assembly, the TSA may be contracted and/or rewound 328 (for example by dethreading) to a stop position. Optionally, the TSA may include one or more thread stoppers. For example, a thread stopper may include an interference element and/or a protrusion on a rotating shaft (for example mid shaft 412 and/or drive shaft 410) and/or on an end cap (for example actuator cap 424). One or more interference elements may meet at a predefined point in the contraction of the TSA and prevent further relative rotation. For example, the interference elements may prevent rotation in the dethreading direction of the inner shaft with respect to the outer shaft thereby inhibiting further contraction and/or thread lock (for example see interference elements 436 and 434 of FIG. 4A).

Figure 6A:
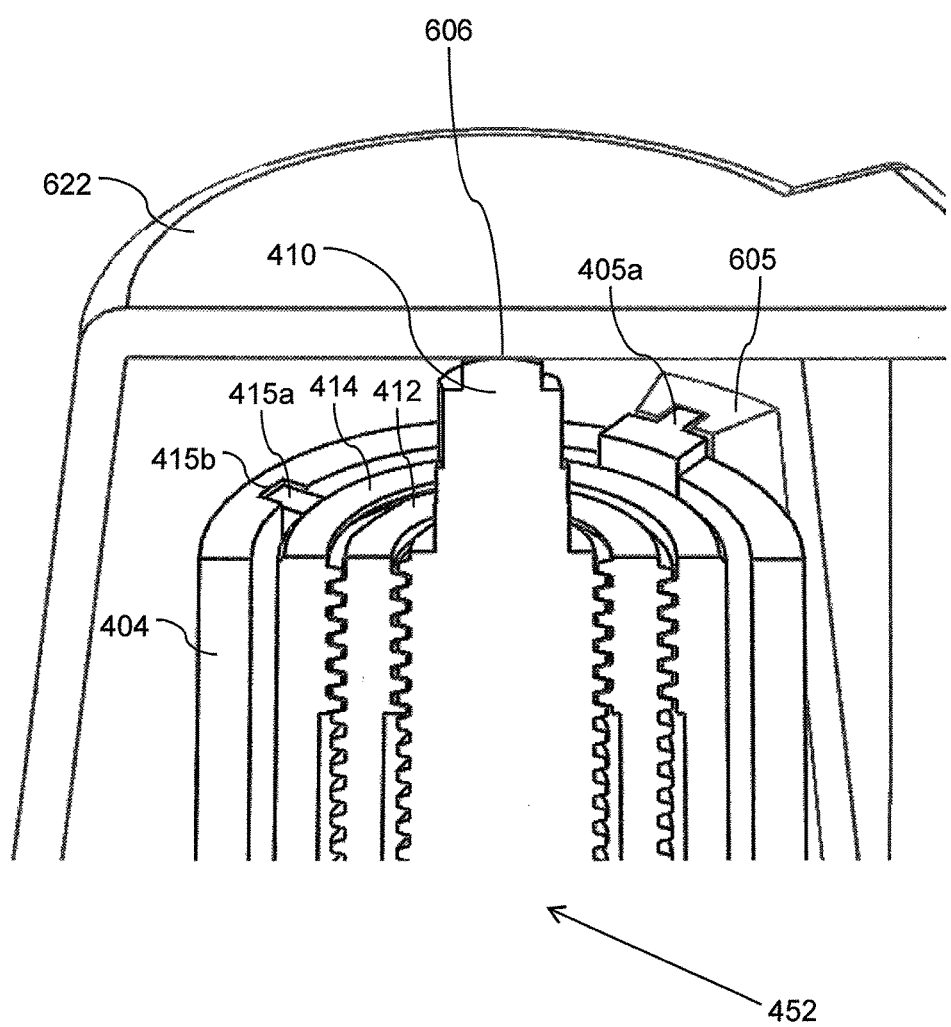
FIG. 6A is a close up cross sectional view of a stopper driver stabilized by a device housing in a retracted configuration in accordance with an embodiment of the present invention.
Figure 6B:
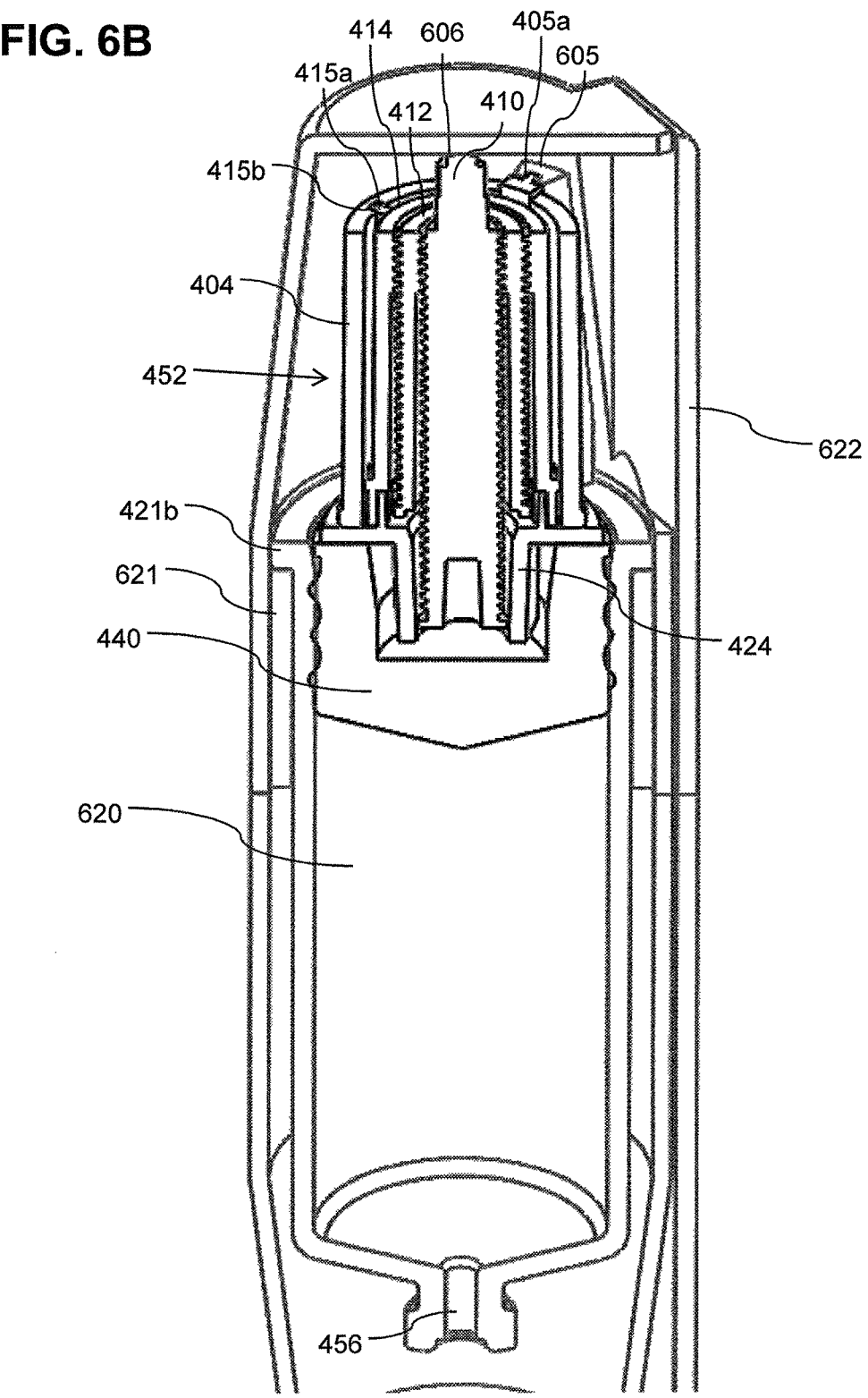
FIG. 6B is a cross sectional view of a reservoir and a stopper driver stabilized by a device housing in a retracted configuration in accordance with an embodiment of the present invention.

In some embodiments a stopper driver is attached to a drug reservoir to form a cartridge. For example, a linear stabilizer (for example stabilizer 402) may be attached to the reservoir (for example, connectors 421a may be attached to flange 421b as illustrated in FIGS. 4A and 4C). A connector that inhibits linear movement of linear stabilizer may be called a linear connector. For example linear connector 421a inhibits linear movement of stabilizer 402 with respect to cartridge 420. Alternatively or additionally, the stopper driver and/or the linear stabilizer may be attached to the housing of a drug delivery device (for example as illustrated in FIGS. 6A-6C).

In some embodiments before inserting the cartridge into a drug delivery device, the TSA may be extended 314 to contact the stopper in the reservoir. Contacting the stopper with the TSA before engaging the TSA to the delivery device may make it easy to determine the volume of drug injected (based on the distance that the stopper has moved which may be proportional to the number of revolutions of the motor and/or drive shaft [for example the pitch of the threading on all of the shafts may be adjusted so that the ratio of revolutions to volume discharged is constant]). Alternatively or additionally, in some embodiments, the reservoir and/or the stopper driver and/or a complete cartridge may be inserted into a drug delivery device before the TSA has contacted the stopper. For example the motor of the drug delivery device may first drive the drive shaft to expand 314 the TSA until it contacts the stopper and then continue to drive the drive shaft to discharge the drug. Allowing the TSA to not contact the stopper until after insertion in the drug delivery device optionally simplifies production and or shipping of the cartridge. In some embodiments, the drug delivery device may deliver the entire content of the cartridge without tracking the quantity delivered. For example in some cases a cartridge may include exactly one dose. In some embodiments, the drug delivery device may include a sensor (for example a load sensor) that senses when the TSA is expanding 314 toward the stopper and/or when the TSA engages the stopper and/or when the TSA is pushing the stopper against a resistance (for example discharging the drug). Alternatively or additionally, the stopper may be placed into the reservoir in an exact position such that the TSA contacts the stopper exactly upon installation. For example it may be unnecessary to expand 314 the TSA after installation to contact the stopper.

In some embodiments, an anti-rotational guide is attached 322 to a housing of the drug delivery device. For example, in FIG. 4D when the cartridge is inserted into the device, connectors 421a fit into slots 421c preventing rotation of stabilizer 402 with respect to a housing of a drug delivery device 422 and/or a motor 408 (for example see FIG. 4E) attached thereto. In some embodiments when cartridge 453 is inserted into delivery device 422, housing 422 may engage the cartridge. For example interference elements 439 may snap to cartridge 453 and/or retain cartridge 453 in the delivery devices. Alternatively or additionally, an anti-rotational guide may be attached to the reservoir and/or the reservoir may be attached to the housing and/or motor of the delivery device. A connector that inhibits rotational movement of an anti-rotational stabilizer may be called an anti-rotational connector. For example anti-rotational connector 421a inhibits rotational movement of stabilizer 402 with respect to the housing deliver device 422.

A Stopper Driver with Sliding Sleeve Anti-Rotational Guide

Referring now to FIG. 4A, the figure is an exploded illustration of an embodiment of a reservoir and a stopper driver including sliding sleeves in a reverse extended state.

In some embodiments a reservoir 420 is supplied sealed with a stopper 440. Optionally reservoir 420 is prefilled and/or stopper 440 is sealed in place using standard filling equipment. In some embodiments, a stopper driver 450 may be assembled from simple and/or snap together parts.

In some embodiments a reservoir 420 may include a proximal opening 454, and/or a distal opening 456. Stopper 440 optionally seals the cavity of reservoir 420. Optionally the stopper may be placed at an arbitrary longitudinal position depending on, for example the volume of the drug distal to stopper 440 and/or space needed for the contracted stopper driver proximal to stopper 440.

In some embodiments, reservoir 420 may include a distal opening 456 and/or a proximal opening 454. For example, proximal opening 454 may be large enough to insert stopper 440. Optionally, distal opening may be configured with a neck and/or a mount for a needle and/or a septum.

In some embodiments, stopper driver 450 includes a TSA 452. TSA 452 is optionally assembled from the reverse expanded state (e.g. as illustrated in FIG. 4A). For example, the proximal end of drive shaft 410 is inserted into mid-shaft 412 until external screw threads 411a of drive shaft 410 engage internal threads 411b near the proximal end of mid shaft 412. Optionally drive shaft 410 is threaded through mid shaft 412 until the proximal end of drive shaft 410 projects out the proximal end of mid shaft 412. Optionally, the proximal end of the combined assembled mid shaft 412 and/or drive shaft 410 is inserted into pushing shaft 414 until external screw threads 413a of mid shaft 412 engage internal threads 413b near the proximal end of pushing shaft 414. Optionally mid shaft 412 is threaded through pushing shaft 414 until the proximal end of drive shaft 410 projects out the proximal end of pushing shaft 414. Optionally a locking and/or snap element prevents TSA 452 from becoming disassembled. For example, a distal cap 424 may include an interference element which locks (e.g. snap fits) to a constraining element, for example a hole in pushing shaft. Alternatively or additionally distal cap 424 may prevent de-threading of the TSA 452. For example, once distal cap 424 is in place, when drive shaft 410 is de-threaded from mid-shaft 412, a receptor on distal cap 424 blocks further movement by a matching interference element thread lock protector on pushing shaft 414 inhibiting further de-threading. For example once distal cap 424 is in place, when mid shaft 412 is de-threaded from pushing shaft 414, an interference element thread lock protector interference element 436 on the distal end of mid shaft 412 is blocked by a matching interference element on distal cap 424 inhibiting further de-threading. Optionally, a TSA may include more than three shafts. For example there may be more than 1 mid shaft. In some embodiments drive shaft 410 may be an inner shaft and pushing shaft 414 may be an outer shaft. Optionally or additionally a drive shaft may be an outer shaft and a pushing shaft may be an inner shaft. In some embodiments, the assembled TSA 452 is assembled into a stopper driver 450.

In some embodiments, TSA 452 is engaged to an anti-rotational guide and/or a transmission element. For example, a coupling including a projection 415a engaged to a track 415b may link pushing shaft 414 to an anti-rotational guide 404. Anti-rotational guide is optionally engaged to a stabilizer 402. For example, a projection 405a of anti-rotational guide 404 may be engaged to a track 405b (for example see FIG. 4B) in stabilizer 402. Optionally, pushing shaft 414, anti-rotational guide 404 and/or stabilizer 402 are slidably engaged. For example, pushing shaft 414, anti-rotational guide 404 and/or stabilizer 402 may slide axially with respect to each other, but are inhibited from rotating one with respect to the other around the axis. In some embodiments, guide elements may snap together. For example, track 415b and/or track 405b may include an interference element (for example at a distal end thereof and/or at a proximal end thereof). Projection 415a is optionally inserted over the distal interference element into track 415b by elastically deforming anti-rotational guide 404 as projection 415a is inserted. Once projection 415a is inside track 415b, anti-rotational guide 404 optionally returns to its original shape and/or projection 415a is inhibited from exiting track 415b by the interference element. Alternatively or additionally, pushing shaft 414 may be elastically squeezed to retract projections 415a at they are fit into track 415b. Projection 405a is optionally inserted over the distal interference element into track 405b by elastically deforming anti-stabilizer 402 as projection 405a is inserted. Once projection 405a is inside track 405b, stabilizer 402 optionally returns to its original shape and/or projection 405a is inhibited from exiting track 405b by the interference element. Alternatively or additionally, rotational guide 404 may be elastically squeezed to retract projections 405a at they are fit into track 405b.

In some embodiments, once TSA 452 is connected its anti-rotational guides (for example anti-rotational guide 404 and/or stabilizer 402) the guides are slid together and/or collapsed such that the proximal end of drive shaft 410 projects out of a proximal opening 403 in stabilizer 402 and/or until a coupler (for example a shoulder bearing 406) of drive shaft 410 rests against stabilizer 402. Optionally, drive shaft 410 rotates freely inside of opening 403. Optionally the transmission element includes for example a cartridge gear 426. The transmission element is optionally engaged to the projecting proximal portion of drive shaft 410. For example, a non-rotational fitting 432a may be inserted through a slot and/or a receptor 432b of cartridge gear 426 such that drive shaft 410 is firmly engaged and/or aligned to gear 426 and/or rotates with gear 426. Optionally a fastener and/or a snap element prevent disassembly of stopper driver 450. For example an end cap 438 may snap to a retainer 437 which may hold to a fastener 430 on the proximal end of drive shaft 410 in FIG. 4A. In some embodiments, the assembled stopper driver 450 is rewound for example by rotating gear 426 with respect to stabilizer 402 and/or drive shaft 410 is rotated with respect to pushing shaft 414. Optionally rotation is in a direction to de-thread TSA 452 until it has contracted and/or until de-threading is stopped by thread stopping elements. The contracted stopper driver 450 is optionally attached to reservoir 420 to form a cartridge 453 (for example see FIG. 4C).

Figure 4B:
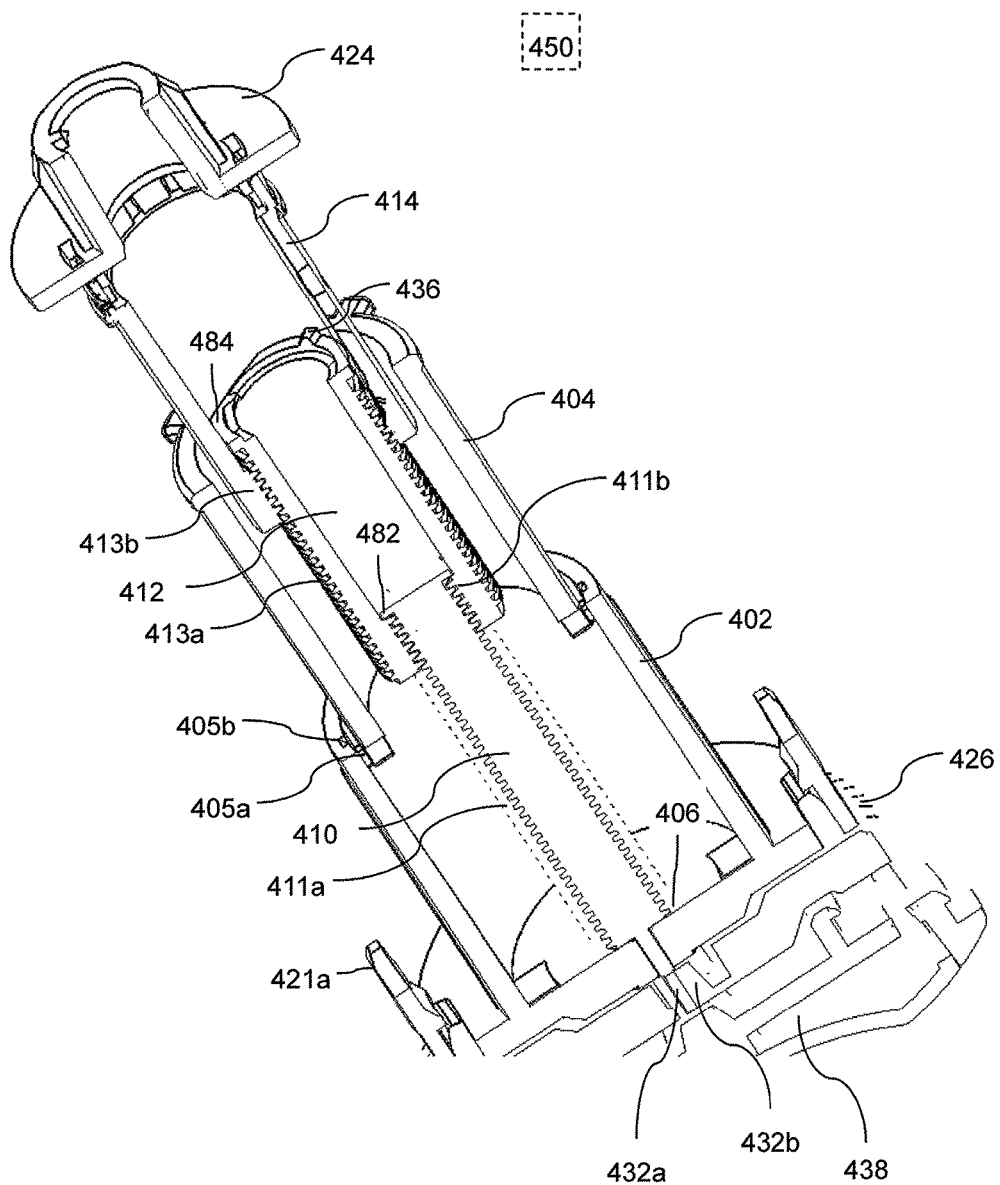
FIG. 4B is cross sectional view of a stopper driver including sliding sleeves in an extended configuration in accordance with an embodiment of the present invention.
Figure 4C:
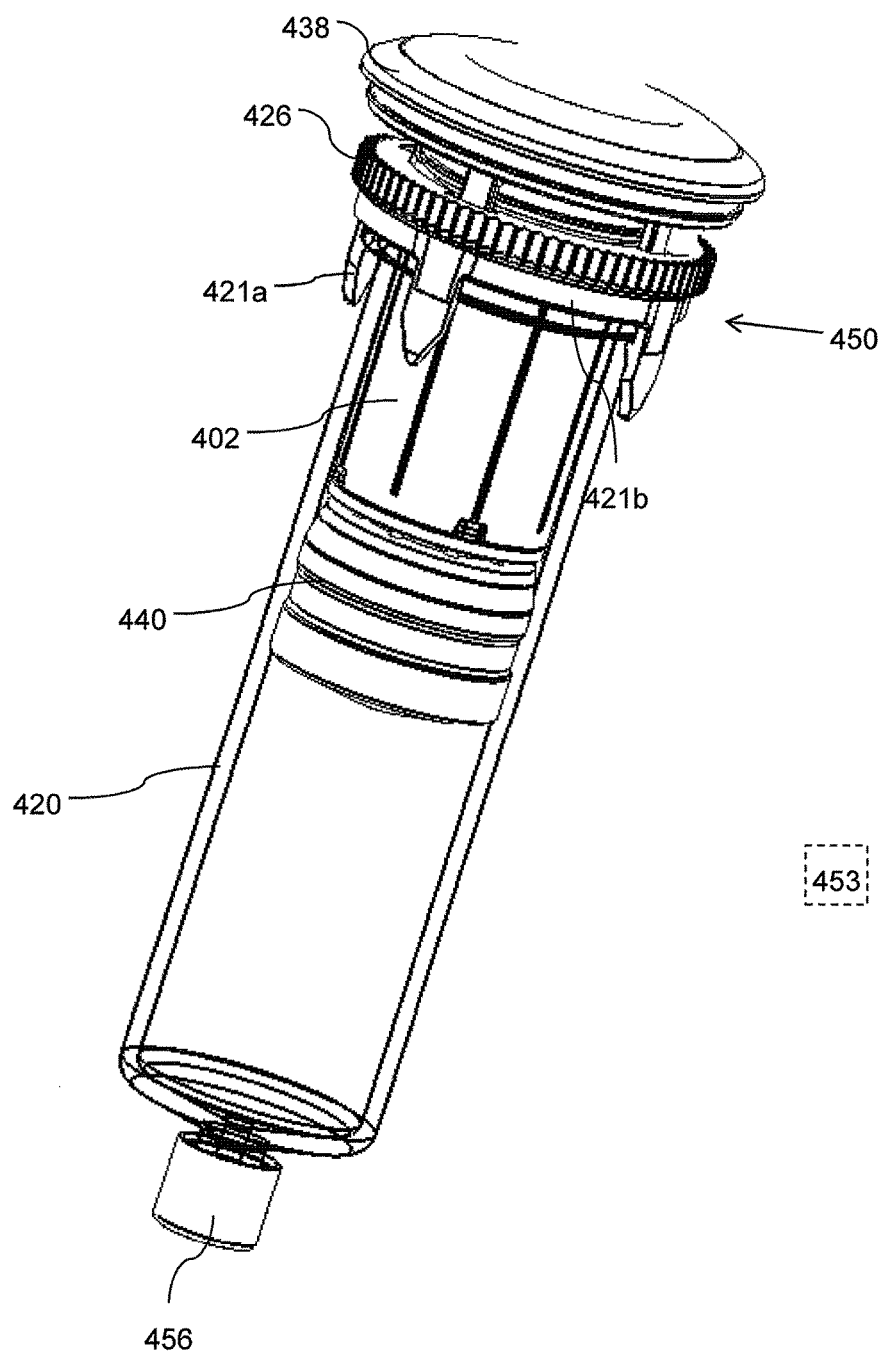
FIG. 4C is a perspective view of a reservoir and a stopper driver including sliding sleeves in an retracted configuration in accordance with an embodiment of the present invention.

Referring now to FIG. 4B, the figure is a cross sectional illustration of an embodiment of stopper driver 450 in an extended state. For example, after assembly of stopper driver 450, cartridge gear 426 is rotated with respect to stabilizer 402 and/or drive shaft 410 is rotated with respect to pushing shaft 414. Optionally rotation is in a direction to thread drive shaft 410 and/or mid shaft 412 proximally through the proximal end of pushing shaft 414 thereby expanding TSA 452 into an extended configuration, for example as illustrated in FIG. 4B.

In some embodiments a shaft may include a member to prevent disengagement of the shaft during over threading and/or over extension of the TSA. For example drive shaft 410 includes a rear flange 482 and mid shaft 412 includes a rear flange 484. When shaft 410 reaches full extension, flange 482 optionally contacts interior threads 411b of mid shaft 412 preventing further extension. When shaft 412 reaches full extension, flange 484 optionally contacts interior threads 413b of pushing shaft 414 preventing further extension. Alternatively or additionally an element to prevent disengagement of shafts due to over extension (for example flange 482 and/or 484). Optionally the element preventing over extension may include an interference element and/or a protrusion and/or another element of any geometry for example an annular element.

In some embodiments, a linear stabilizer will block movement of a drive shaft in a proximal direction. For example, shoulder bearing 406 is supported against stabilizer 402. Optionally, drive shaft 410 can rotate with respect to stabilizer 402 around the longitudinal axis of stopper driver 450 but is inhibited from moving axially in a proximal direction with respect to stabilizer 402.

FIG. 4C is a perspective view of a cartridge 453 including reservoir 420, stopper 440 and/or stopper driver 450 in accordance with an embodiment of the present invention. In some embodiments, the assembled stopper driver 450 may be attached to reservoir 420. For example, connectors 421a may clip stabilizer 402 onto rear flange 421b of reservoir 420. Optionally, stabilizer 402 is a linear stabilizer linearly stabilizing and/or retaining TSA 452 inside the cavity of reservoir 420 and/or inhibiting proximal movement of driver 410 (for example by means of shoulder bearing 406 as illustrated in FIG. 4B). When TSA 452 is expanded pusher shaft 414 moves distally with respect to stabilizer 402 and/or reservoir 420 until pusher shaft 414 contacts stopper 440. Further expansion of TSA 452 pushes stopper 440 distally and/or discharges the drug.

In some embodiments, Cartridge 453 is inserted as a single element into a drug delivery device. Optionally, when stopper driver 450 is installed to cartridge 453 in a contracted state, a large portion of driver 450 (for example ranging between 50% to 75% and/or ranging between 75% to 90% and/or ranging between 90% to 100%) is positioned inside reservoir 420. Alternatively or additionally most or all of the stopper driver may be on the outside of the reservoir when the driver is in a contracted state and/or when the driver is attached to the reservoir.

Figure 4D:
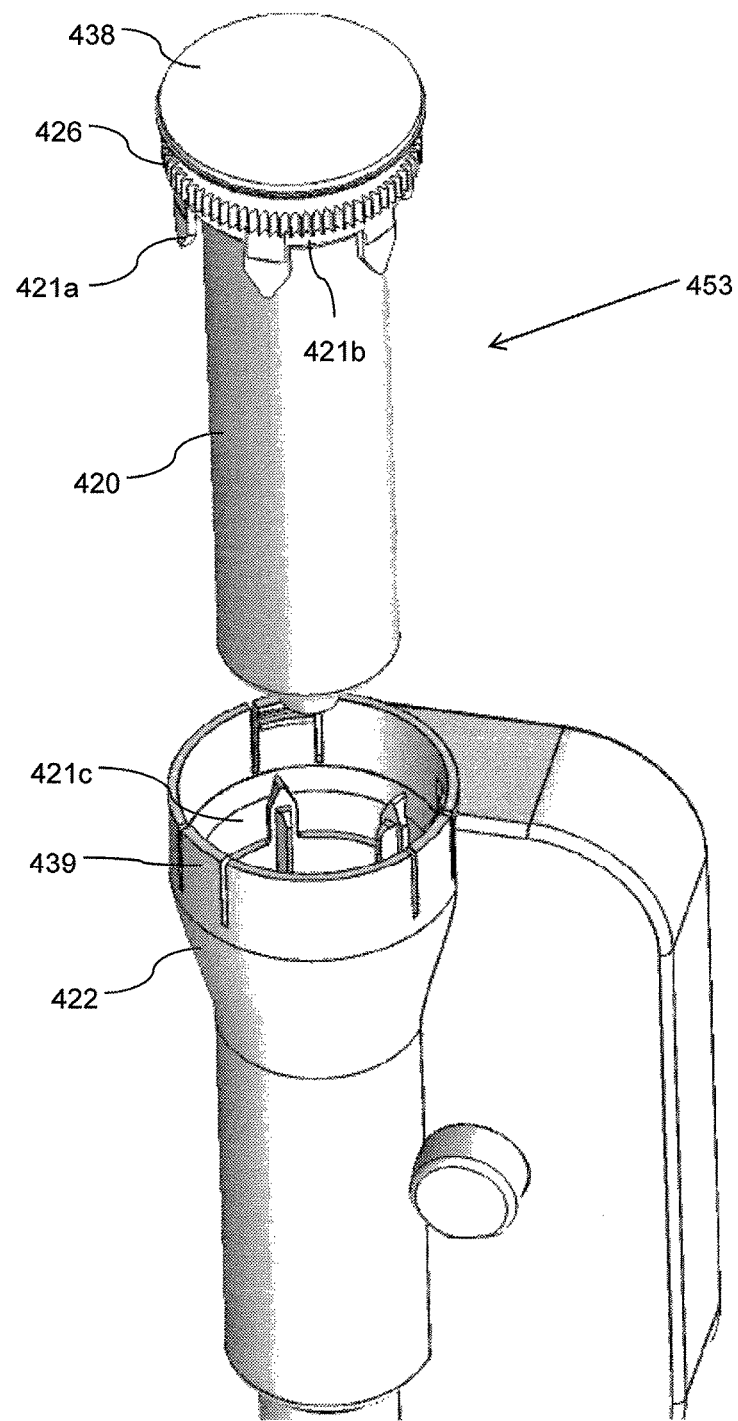
FIG. 4D is a perspective view of insertion of a cartridge including a stopper driver and a reservoir into a drug delivery device in accordance with an embodiment of the present invention.

FIG. 4D is a perspective view of insertion of cartridge 453 into a drug delivery device 422 in accordance with an embodiment of the present invention. In some embodiments, inserting a cartridge into drug delivery device 422 will open a fluid flow path between reservoir 420 and device 422 and/or engage a transmission element of cartridge 453 to a motor of device 422 and/or rotationally stabilize the cartridge. For example, cartridge 453 is inserted linearly into a guide path in device 422. As cartridge 453 is inserted, a cannula inside device 422 pierces a septum on the distal end of cartridge 453 creating a fluid path between device 422 and reservoir 420. Alternatively or additional, a cannula on the distal end of cartridge 453 may pierce a septum of device 422 forming the fluid path. Alternatively or additional, a hypodermic needle on the distal end of cartridge 453 be inserted directly into a subject.

In some embodiments, linear stabilizer 402 (as explained above) is also an anti-rotational stabilizer 402. Optionally, stabilizer 402 connects directly to device 422 to compensate for torque applied by a motor 408 to cartridge gear 426 without applying significant torque to reservoir 420. For example, connectors 421a of stabilizer 402 fit into slots 421c in drug delivery device 422. Slots 421c prevent stabilizer 402 from rotating with respect to device 422. Slots 421c are angled to lead connectors 421a and/or rotationally align cartridge 453. For example cartridge 453 may be inserted into device 422 without require angular alignment by the operator. Alternatively or additionally a cartridge may have a specific insertion alignment. In some embodiments, a linear stabilizer may be separate from an anti-rotational stabilizer.

Figure 4E:
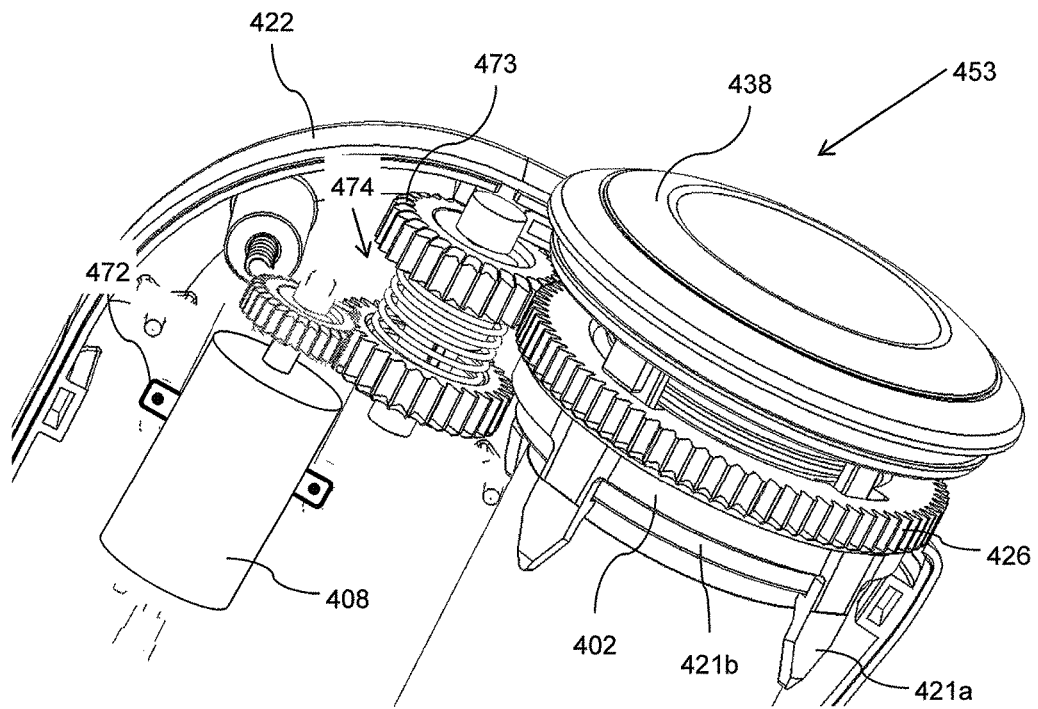
FIG. 4E is a perspective view of a linkage between a cartridge and a motor of a drug delivery device in accordance with an embodiment of the present invention.

FIG. 4E is a perspective view of a linkage between a stopper driver and a motor of a drug delivery device in accordance with an embodiment of the present invention. As cartridge 453 is inserted into drug delivery device 422, gear 426 optionally slides into engagement and/or meshes with a transmission 474 (for example including a drive gear 473). Transmission 474 and/or drive gear 473 are optionally driven by a motor 408. In some embodiments motor mounts 472 may connect motor 408 to the housing of the drug delivery device 422. For example, as the motor applies torque to transmission 474, the body of motor 408 is anti-rotationally stabilized against the housing of device 422 by motor mounts 472. Optionally, anti-rotational torque is transferred by the housing of device 422 and/or connectors 421a to anti-rotational stabilizer 402 and/or anti-rotational guide 404 and/or pushing shaft 414 (for example as explained herein above).

A Stopper Driver with Sliding Post Anti-Rotational Guide

Figure 5A:
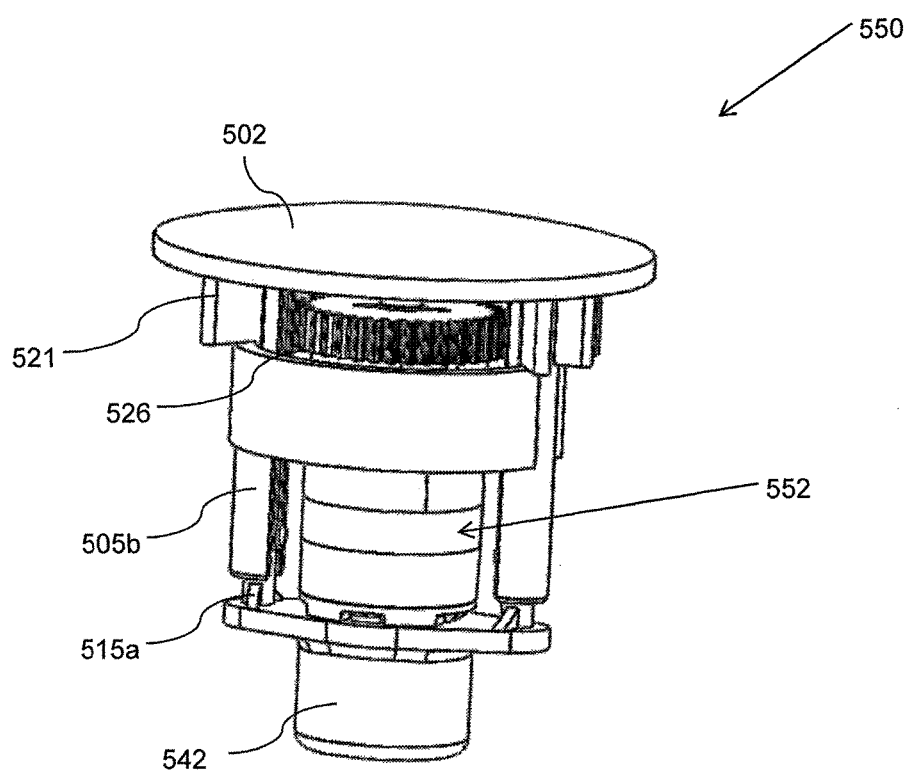
FIG. 5A is a perspective view of a stopper driver including sliding post anti-rotational guides in a retracted configuration in accordance with an embodiment of the present invention.

FIG. 5A is a perspective view of a stopper driver 550 including sliding post anti-rotational guides in a retracted configuration in accordance with an embodiment of the present invention. Optionally, an anti-rotational stabilizer 502 is connected to a stopper adapter 542 by a guide assembly including hollow guide tracks 505b and/or sliding posts 515a. In some embodiments, a cartridge gear 526 drives a TSA 552. Optionally connectors 521 connect anti-rotational stabilizer 502 to a drug delivery device. For example, the driver may be slid longitudinally into a drug delivery device. Optionally cartridge gear 526 meshes to a transmission of the device and/or connectors 521 slide into slots in the device. Torque is optionally supplied to gear 426 for example to extend TSA 552 and/or to push a stopper. In some embodiments, anti-rotational stabilization is supplied to connectors 521 and/or guide elements (for example stabilizer 502, track 505b and/or post 515a).

Figure 5B:
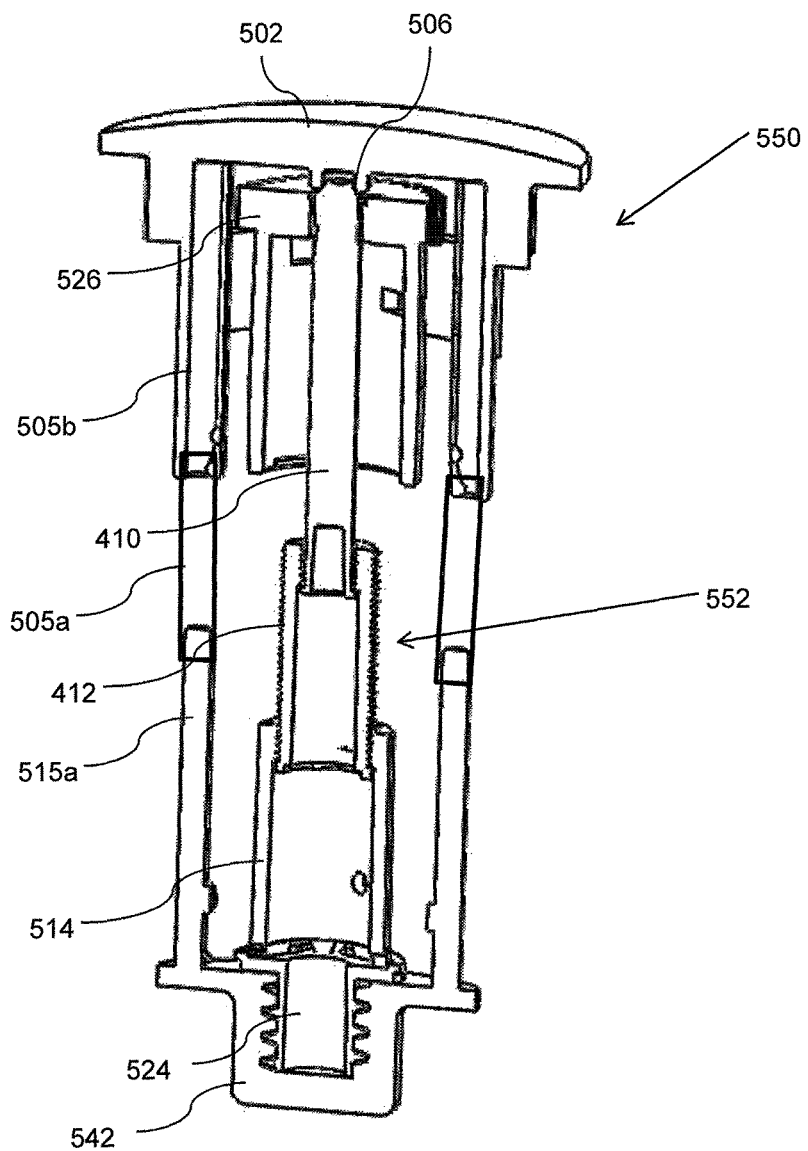
FIG. 5B is a cross sectional view of a stopper driver including sliding post anti-rotational guides in an extended configuration in accordance with an embodiment of the present invention.

FIG. 5B is a cross sectional view of stopper driver 550 in an extended configuration in accordance with an embodiment of the present invention. TSA 552 optionally includes a proximal drive shaft 410, a mid shaft 412 and/or a distal stopper pushing shaft 514. For example stopper adapter 542 and/or posts 515a link pushing shaft 514 to a sliding guide post 505a and/or fixed guide track 505b and/or stabilizer 502. The assembled TSA 552 may optionally be held together by a distal end cap 524. The anti-rotational guides of driver 550 optionally include telescoping posts, for example an inner post 515a may slide into a hollow mid post 505a which may slide into a hollow track 505b. Drive shaft 410 is optionally linearly stabilized by a coupler, for example a shoulder bearing 506. Bearing 506 optionally rest on stabilizer 502.

A Stopper Driver with Anti-Rotational Guide Stabilized by the Device Housing

FIG. 6A is a close up cross sectional view of a stopper driver stabilized by a device housing in a retracted configuration in accordance with an embodiment of the present invention. In some embodiments, TSA 452 is stabilized by a housing of a drug delivery device 622. For example, projection 405a of anti-rotational guide 404 connects to a guide track 605 that is attached to and/or intrinsic to the housing of device 622. Drive shaft 410 is optionally linearly stabilized against the housing of device 422. For example, linear stabilization may be via a coupler (for example a bearing 606). For simplicity the transmission and motor assembly are not shown in the FIGS. 6A-6C.

FIG. 6B is a perspective view of a reservoir and a stopper driver stabilized by a device housing in a retracted configuration and engaged with stopper 440 and reservoir 620 in accordance with an embodiment of the present invention. For example, reservoir 620 may be shorter than reservoir 420. In the contracted state, TSA 452 remains outside of the distal end of reservoir 420. Optionally, in the embodiment of FIGS. 6A-6C, reservoir 620 and TSA 452 are built into drug delivery device 622 rather than being inserted as a cartridge into the device by a user. The housing of device 622 optionally includes a shoulder 621 which linearly stabilizes reservoir 620 (for example locking it in an axial position with respect to the housing). For simplicity, the fluid path connecting distal opening 456 to device 622 is not shown in the FIGS. 6A-6C.

FIG. 6C is a perspective view of a reservoir and a stopper driver stabilized by a device housing in a retracted configuration in accordance with an embodiment of the present invention. Optionally drive shaft 410 is rotated expanding TSA 452. For example TSA 452 expands into reservoir 620 and/or pushes stopper 440 into reservoir 620 and/or discharges a drug from reservoir 620. Optionally as TSA 452 expands, an anti-rotational guide moves into reservoir 620. For example projection 405a may slide down track 605 as anti-rotation guide 404 may slide into reservoir 620 and/or projection 415a may slide down track 415b as pushing shaft 414 slides with respect to anti rotation guide 404.

Exemplary Dimensions of a Drug Delivery Device

In some embodiments the payload of a reservoir (for example a syringe) may include, for example between 0.5 and 3 ml and/or between 3 and 6 ml and/or between 6 and 10 ml and/or between 10 and 15 ml of a drug and/or more. In some embodiments, the injector may discharge the entire payload as a single dose. A drug delivery device may include, for example, a pen injector and/or a patch injector, and/or an internally powered driver to drive the stopper and/or discharge the payload. The reservoir of the injector may be oriented parallel to the skin of a subject and/or perpendicular to the skin and/or at an angle between parallel and perpendicular, for example between 60 to 90 degrees and/or between 30 to 60 degrees and/or between 0 to 30 degrees. For the sake of this application an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example the driver may be designed to discharge the payload over a time period ranging between 20 and 120 seconds and/or between 120 and 600 seconds and/or between 600 and 7200 seconds and/or longer. In some embodiments, discharge may be driven by a driver. An internally powered driver may be powered by various mechanisms including for example a motor (including for example a DC motor, an actuator, a brushless motor) and/or a transmission including for example a telescoping assembly and/or a threaded element and/or a gear and/or a coupling and/or an elastic mechanism (for example a spring and/or a rubber band) and/or an expanding gas and/or a hydraulic actuator).

A drug delivery device in accordance with some embodiments of the current invention may include reservoir. For example a reservoir may include a medicine container and/or a standard type syringe. Optionally a standard type syringe may be preloaded with medicine using standard equipment and/or in an aseptic room. A preloaded standard type syringe may optionally include a proximal opening. A stopper may optionally seal the proximal opening and/or protect the sterility of the contents of the syringe. A sterile needle (for example a hollow needle) may optionally be connected to the syringe barrel. For example, the hollow of the needle may be in fluid communication with the interior of the barrel. The needle may optionally be rigidly attached to the distal end of the barrel. The sterility of all and/or part of the needle may for example be protected by a sterile cover. The sterile cover may remain on the needle when the syringe is supplied and/or installed into an injector. For example, the medicine container may optionally include a cylindrical barrel rigidly attached to a needle. Optionally, the long axes of the needle and barrel of the syringe may be parallel and/or coaxial. Optionally, the needle may be mounted on the distal end of the barrel. Optionally the needle point may be pointing in the distal direction. In some embodiments a stopper may slide axially along the inside of the barrel to discharge a medicine payload. For example, the medicine may be discharged through the hollow needle.

In some embodiments, a TSA may produce a force ranging for example between 0.02 to 0.2 N and/or between 0.2 and 0.5 N and/or between 0.5 to 5 N and/or between 5 to 60 N and/or between 60 to 90 N. For example the force required to inject the drug may depend on the injection rate and/or the viscosity of the drug and/or the syringe geometry and/or the needle dimensions.

In some embodiments, the stress to inject a medicine may include a torque. For example, injection of medicine may be driven by a stopper. The stopper may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 3 and 15 mm. The torque to power injection may range for example between 0.2 and 1.0 N*cm.

During injection, the linear movement of a stopper may range for example between 5-40 mm and/or between 40-50 mm. The length of movement of the stopper may vary for example with the volume of medicine to be injected that may range for example between 0.5 to 3 ml and/or between 3 to 10 ml.

It is expected that during the life of a patent maturing from this application many relevant technologies will be developed and the scope of the terms is intended to include all such new technologies a priori.

As used herein the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An assembly for driving a stopper in a drug reservoir of a drug delivery device, the assembly comprising:
    an anti-rotational stabilizer anti-rotationally coupled to a housing of the drug delivery device;
    a stopper adapter configured to engage the stopper of the drug reservoir;
    a telescoping assembly that telescopes by relative rotation between at least a proximal shaft and a distal shaft oriented along an axis of said reservoir; the proximal shaft being linearly stabilized by a shoulder bearing of the anti-rotational stabilizer, said shoulder bearing preventing movement of said proximal shaft in a proximal direction with respect to the anti-rotational stabilizer while permitting rotation of said proximal shaft with respect to the anti-rotational stabilizer and the distal shaft being in engagement with the stopper adapter; and;
    anti-rotational guides including telescoping posts anti-rotationally extending between the anti-rotational stabilizer and the stopper adapter,
    wherein rotating said proximal shaft with respect to said anti-rotational stabilizer moves said distal shaft and said stopper adapter along said axis, thereby slidably expanding the anti-rotational telescoping posts.

2. The assembly of claim 1, further comprising:
an intermediate shaft threadably engaged to said proximal shaft and to said distal shaft such that said telescoping assembly also telescopes by rotating said proximal shaft with respect to said intermediate shaft.

3. The assembly of claim 2, wherein a maximum axial movement of said distal shaft with respect to the reservoir is greater than a maximum axial movement of said intermediate shaft with respect to the reservoir.

4. The assembly of claim 1, wherein said anti-rotational guides include a guide track.

5. An assembly for driving a stopper in a drug reservoir of a drug delivery device, the assembly comprising:
a telescoping assembly that telescopes by relative rotation between at least a proximal shaft and a distal shaft oriented along an axis of said reservoir; said distal shaft configured to engage the stopper of the drug reservoir;
an anti-rotational guide sized to move along said axis of the reservoir; said anti-rotational guide slidably and anti-rotationally coupled to a housing of the drug delivery device;
a coupling slidably and anti-rotationally linking said anti-rotational guide to said distal shaft; said sliding and anti-rotation with respect to said axis of the reservoir such that rotating said proximal shaft with respect to said anti-rotational guide moves said distal shaft along said axis and moves said distal shaft with respect to said anti-rotational guide, said anti-rotational guide also moving along said axis;
a linear stabilizer coupled to said proximal shaft, inhibiting axial movement of said proximal shaft in a proximal direction with respect to said linear stabilizer, said linear stabilizer coupled to the reservoir inhibiting axial movement of said linear stabilizer in a proximal direction with respect to the reservoir, such that said rotation of said proximal shaft causes said distal shaft to advance distally inside of the drug reservoir,
wherein said linear stabilizer includes an anti-rotational connector fitting to said housing for preventing rotation of said linear stabilizer with respect to said housing and wherein said anti-rotational guide slidably engages to said housing by means of said linear stabilizer.

6. The assembly of claim 5, wherein the anti-rotational connector is also shaped to attach to a proximal portion of said reservoir.

7. The assembly of claim 6, wherein said anti-rotational connector is shaped to attach to a flange of said reservoir.

8. The assembly of claim 5, wherein said reservoir and said assembly form a cartridge and wherein said housing includes an opening fitting said cartridge and wherein said anti-rotational connector is shaped to connect to said housing to limit rotation of said anti-rotational connector with respect to said housing when said cartridge is inserted into said opening.

9. The assembly of claim 5, further comprising:
a bearing preventing proximal movement of said proximal shaft with respect to said housing and allowing rotation of said proximal shaft with respect to said housing.

* * * * *